United States Patent
Holl et al.

(10) Patent No.: US 6,712,925 B1
(45) Date of Patent: Mar. 30, 2004

(54) METHOD OF MAKING A LIQUID ANALYSIS CARTRIDGE

(75) Inventors: Mark R. Holl, Seattle, WA (US); Floyd Edwards, Clarence, NY (US); Robert Morff, West Chester, OH (US); Gerald L. Klein, Edmonds, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/428,804

(22) Filed: Oct. 28, 1999

Related U.S. Application Data

(62) Division of application No. 09/080,691, filed on May 18, 1998, now abandoned.

(51) Int. Cl.[7] .............................................. B32B 31/04
(52) U.S. Cl. ................... 156/292; 156/257; 156/272.8; 219/121.69; 219/121.71
(58) Field of Search ................................. 156/245, 247, 156/248, 256, 257, 272.8, 273.3, 275.7, 292; 219/121.67, 121.68, 121.69, 121.7, 121.71, 121.72; 204/451, 601; 137/884

(56) References Cited

U.S. PATENT DOCUMENTS

| | | | |
|---|---|---|---|
| 3,463,614 A | 8/1969 | Leslie | 23/230 |
| 3,677,710 A | 7/1972 | Hirsch | 23/258.5 |

(List continued on next page.)

FOREIGN PATENT DOCUMENTS

| | | |
|---|---|---|
| DE | 25 21 236 A1 | 11/1976 |
| EP | 0 288 029 A2 | 10/1988 |
| EP | 0 294 701 B1 | 9/1992 |
| EP | 0 381 501 B1 | 6/1994 |

(List continued on next page.)

OTHER PUBLICATIONS

Alonso et al., "Time–dependent rheological behavior of blood flow at low shear in narrow horizontal tubes," *Biorheology* 26(2):229–246, 1989.

(List continued on next page.)

*Primary Examiner*—Jeff H. Aftergut
*Assistant Examiner*—John T. Haran
(74) *Attorney, Agent, or Firm*—Seed IP Law Group PLLC

(57) ABSTRACT

The present invention provides an apparatus and method for storing a particle-containing liquid. The storage apparatus comprises a microfluidic convoluted flow channel having a plurality of particle capture regions. The storage channel is preferably an isotropic spatially periodic channel. Sedimented particles can be resuspended following storage. This invention further provides a microfluidic analysis cartridge having a convoluted storage channel therein. The sample analysis can use optical, electrical, pressure sensitive, or flow sensitive detection. A plurality of analysis channels can be included in a single cartridge. The analysis channels can be joined to reagent inlets for diluents, indicators or lysing agents. A mixing channel can be positioned between the reagent inlet and the analysis region to allow mixing and reaction of the reagent. The cartridge can include additional valves and pumps for flow management. The analysis cartridge can be a self-contained disposable cartridge having an integral waste storage container. This invention further provides a sheath flow assembly. The sheath flow assembly includes a sample channel and first and second sheath fluid channels positioned on either side of and converging with the sample channel. The assembly also includes upper and lower sheath fluid chambers positioned above and below and converging with the sample channel. The flow cartridges of this invention can be formed by molding, machining or etching. In a preferred embodiment they are laminated. This invention further provides a method of fabricating a laminated microfluidic flow device. In the method, flow elements are formed in rigid sheets and abutting surfaces of the sheets are bonded together.

10 Claims, 18 Drawing Sheets

U.S. PATENT DOCUMENTS

| | | | | |
|---|---|---|---|---|
| 3,811,474 A | * | 5/1974 | Bauer et al. | 137/833 |
| 4,109,505 A | | 8/1978 | Clark et al. | 73/1 R |
| 4,201,470 A | | 5/1980 | Ehrly et al. | 356/39 |
| 4,206,650 A | | 6/1980 | Berber et al. | 73/421 R |
| 4,473,424 A | * | 9/1984 | Sorko-Ram | 156/272.8 |
| 4,484,134 A | | 11/1984 | Halloran | 324/71.1 |
| 4,503,385 A | | 3/1985 | Haynes | 324/71.4 |
| 4,533,638 A | | 8/1985 | Murányi et al. | 435/288 |
| 4,623,470 A | | 11/1986 | Adler | 210/787 |
| 4,726,929 A | | 2/1988 | Gropper et al. | 422/68 |
| 4,766,079 A | | 8/1988 | Fele et al. | 436/63 |
| 4,781,459 A | | 11/1988 | Suzuki | 356/335 |
| 4,793,485 A | | 12/1988 | Bertolotti | 356/318 |
| 4,818,103 A | | 4/1989 | Thomas et al. | 356/72 |
| 4,822,568 A | | 4/1989 | Tomita | 422/73 |
| 4,894,146 A | | 1/1990 | Giddings | 209/12 |
| 4,908,112 A | | 3/1990 | Pace | 204/299 R |
| 4,938,592 A | | 7/1990 | Poole et al. | 356/335 |
| 4,963,498 A | | 10/1990 | Hillman et al. | 436/69 |
| 4,983,038 A | | 1/1991 | Ohki et al. | 356/246 |
| 5,007,732 A | | 4/1991 | Ohki et al. | 356/73 |
| 5,011,022 A | | 4/1991 | Palepu et al. | 209/155 |
| 5,039,617 A | | 8/1991 | McDonald et al. | 436/69 |
| 5,141,651 A | | 8/1992 | Giddings | 210/748 |
| 5,147,607 A | | 9/1992 | Mochida | 422/57 |
| 5,182,617 A | | 1/1993 | Yoneyama et al. | 356/440 |
| 5,225,163 A | | 7/1993 | Andrews | 422/61 |
| 5,240,618 A | | 8/1993 | Caldwell et al. | 210/748 |
| 5,250,263 A | | 10/1993 | Manz | 422/81 |
| 5,254,201 A | * | 10/1993 | Konda et al. | 156/344 |
| 5,260,029 A | | 11/1993 | Hosoi et al. | 422/82.08 |
| 5,288,463 A | | 2/1994 | Chemelli | 422/58 |
| 5,370,842 A | | 12/1994 | Miyazaki et al. | 422/82.06 |
| 5,376,252 A | * | 12/1994 | Ekstrom et al. | 204/603 |
| 5,464,752 A | | 11/1995 | Kortright et al. | 435/7.24 |
| 5,480,614 A | | 1/1996 | Kamahori | 422/70 |
| 5,500,071 A | | 3/1996 | Kaltenbach et al. | 156/272.8 |
| 5,500,187 A | | 3/1996 | Deoms et al. | 422/58 |
| 5,530,540 A | | 6/1996 | Wyatt et al. | 356/246 |
| 5,579,107 A | | 11/1996 | Wright et al. | 356/336 |
| 5,585,069 A | | 12/1996 | Zanzucchi et al. | 422/100 |
| 5,587,070 A | | 12/1996 | Pall et al. | 210/202 |
| 5,591,403 A | | 1/1997 | Gavin et al. | 422/73 |
| 5,599,503 A | | 2/1997 | Manz et al. | 422/82.05 |
| 5,601,234 A | | 2/1997 | Larue | 239/1 |
| 5,601,727 A | | 2/1997 | Bormann et al. | 210/767 |
| 5,627,041 A | | 5/1997 | Shartle | 435/7.24 |
| 5,635,358 A | | 6/1997 | Wilding et al. | 435/7.2 |
| 5,637,469 A | | 6/1997 | Wilding et al. | 435/7.21 |
| 5,639,423 A | | 6/1997 | Northrup et al. | 122/50 |
| 5,644,395 A | | 7/1997 | Folta | 356/246 |
| 5,656,499 A | | 8/1997 | Chupp et al. | 436/43 |
| 5,665,312 A | | 9/1997 | Sperber et al. | 422/81 |
| 5,674,743 A | | 10/1997 | Ulmer | 435/287.2 |
| 5,681,484 A | | 10/1997 | Zanzucchi et al. | 216/2 |
| 5,690,895 A | | 11/1997 | Matsumoto et al. | 422/73 |
| 5,707,799 A | | 1/1998 | Hansmann et al. | 435/6 |
| 5,716,852 A | | 2/1998 | Yager et al. | 436/172 |
| 5,726,404 A | | 3/1998 | Brody | 200/81 R |
| 5,726,751 A | | 3/1998 | Altendorf et al. | 356/246 |
| 5,728,351 A | | 3/1998 | Carver, Jr. | 422/73 |
| 5,736,100 A | | 4/1998 | Miyake et al. | 422/64 |
| 5,744,366 A | | 4/1998 | Kricka et al. | 436/63 |
| 5,747,349 A | | 5/1998 | van den Engh et al. | 436/172 |
| 5,748,827 A | | 5/1998 | Holl et al. | 385/134 |
| 5,755,942 A | | 5/1998 | Zanzucchi et al. | 204/454 |
| 5,840,254 A | | 11/1998 | Carver, Jr. et al. | 422/68.1 |
| 5,858,187 A | | 1/1999 | Ramsey et al. | 204/452 |
| 5,858,195 A | | 1/1999 | Ramsey | 204/601 |
| 5,863,502 A | | 1/1999 | Southgate et al. | 422/58 |
| 5,868,322 A | | 2/1999 | Loucks, Jr. et al. | 239/418 |
| 5,876,675 A | * | 3/1999 | Kennedy | 422/99 |
| 5,885,470 A | * | 3/1999 | Parce et al. | 216/33 |
| 5,919,711 A | | 7/1999 | Boyd et al. | 436/178 |
| 5,932,100 A | | 8/1999 | Yager et al. | 210/634 |
| 5,945,334 A | * | 8/1999 | Besemer et al. | 435/287.2 |
| 5,948,684 A | | 9/1999 | Weigl et al. | 436/52 |
| 5,971,158 A | | 10/1999 | Yager et al. | 209/155 |
| 5,972,710 A | | 10/1999 | Weigl et al. | 436/34 |
| 5,976,465 A | | 11/1999 | Luzzana et al. | 422/82.03 |
| 5,989,402 A | * | 11/1999 | Chow et al. | 204/450 |
| 5,993,750 A | | 11/1999 | Ghosh et al. | 422/191 |
| 6,007,690 A | | 12/1999 | Nelson et al. | 204/601 |
| 6,027,627 A | | 2/2000 | Li et al. | 204/603 |
| 6,033,628 A | | 3/2000 | Kaltenbach et al. | 422/68.1 |
| 6,073,482 A | | 6/2000 | Moles | 73/53.01 |
| 6,120,666 A | | 9/2000 | Jacobson et al. | 204/452 |
| 6,124,138 A | | 9/2000 | Woudenberg et al. | 436/518 |
| 6,136,272 A | | 10/2000 | Weigl et al. | 422/82.05 |
| 6,139,800 A | | 10/2000 | Chandler | 422/82.08 |
| 6,153,073 A | | 11/2000 | Dubrow et al. | 204/453 |
| 6,156,208 A | | 12/2000 | Desjardins et al. | 210/695 |
| 6,159,739 A | | 12/2000 | Weigl et al. | 436/52 |
| 6,167,910 B1 | * | 1/2001 | Chow | 137/827 |
| 6,171,865 B1 | | 1/2001 | Weigl et al. | 436/52 |
| 6,176,962 B1 | * | 1/2001 | Soane et al. | 156/292 |
| 6,176,991 B1 | | 1/2001 | Nordman | 204/601 |
| 6,183,064 B1 | * | 2/2001 | Murthy et al. | 219/121.67 |
| 6,183,829 B1 | * | 2/2001 | Daecher et al. | 428/64.1 |
| 6,188,474 B1 | | 2/2001 | Dussault et al. | 356/246 |
| 6,221,654 B1 | | 4/2001 | Quake et al. | 435/287.3 |
| 6,221,677 B1 | | 4/2001 | Wu et al. | 436/518 |
| 6,251,615 B1 | | 6/2001 | Oberhardt | 435/7.21 |
| 6,287,438 B1 | | 9/2001 | Knoll | 204/409 |
| 6,319,469 B1 | | 11/2001 | Mian et al. | 422/64 |
| 6,432,630 B1 | | 8/2002 | Blankenstein | 435/4 |
| 6,436,720 B1 | | 8/2002 | Oberbeck et al. | 436/180 |
| 6,576,194 B1 | * | 6/2003 | Holl et al. | 422/81 |
| 2002/0141902 A1 | | 10/2002 | Ozasa et al. | 422/82.09 |
| 2002/0187557 A1 | | 12/2002 | Hobbs et al. | 436/161 |

FOREIGN PATENT DOCUMENTS

| | | |
|---|---|---|
| EP | 0 645 169 A1 | 3/1995 |
| WO | WO 96/04547 | 2/1996 |
| WO | WO 96/12546 | 5/1996 |
| WO | WO 96/14934 | 5/1996 |
| WO | WO 96/34282 | 10/1996 |
| WO | WO 97/02357 | 1/1997 |
| WO | WO 97/39338 | 10/1997 |
| WO | WO 99/29497 | 6/1999 |
| WO | WO 00/70080 | 11/2000 |
| WO | WO 00/74850 | 12/2000 |
| WO | WO 01/09589 | 2/2001 |
| WO | WO 02/11887 | 2/2002 |

OTHER PUBLICATIONS

Elwenspoek, M. et al. (1994) "Towards integrated micorliquid handling systems" *J. Micromech. Microeng.* 4:227–243.

Gravesen, P. et al. (1993) "Microfluidics—a review" *J. Micromech. Miroeng.* 3:168–182.

Kikuchi, Y. et al. (1992) "Optically accessible microchannels formed in a single–crystal silicon substrate for studies of blood rheology" *Microvas. Res.* 44:226–240.

Manz, A. et al. (1993) "Planar chips technology for miniaturization of separation systems: A developing perspective in chemical monitoring," *Advances in Chromatography*, Vol 33, Ch. 1, Pp. 1–67.

Miyake, R. et al. (1991) "A development of microsheath flow chamber" *Proceedings of the IEEE MicroElectro Mechanical Systems Workshop 265–270.*

Petersen, K.E. (1982) "Silicon as a mechanical material" *Proceedings of the IEEE 10(5):420–457.*

Shoji, S. and Esashi, M. (1994) "Microflow devices and systems" *J. Micromech Microeng. 157–171.*

Sobek, D. et al. (1993) "A microfabricated flow chamber for optical measurements in fluids" *Proceedings of the IEEE MicroElectro Mechanical Systems Workshop 219–224.*

Sobek, D. et al. (1994) "Microfabricated fused silica flow chambers for flow cytometry" *Proceedings of Solid–State Sensors and Actuators Workshop, Hilton Head, SC.*

Verpoorte, E. et al. (1992) "A silicon flow cell for optical detection in miniaturized total chemical analysis systems" *Sensors and Actuators 8:66–70.*

Verpoorte, E. M. J. et al. (1994) "Three–dimensional micro flow manifolds for miniaturized chemical analysis systems" *J. Micromech. Microeng. 4:246–256.*

Wilding, P. et al. (1994) "Manipulation and flow of biological fluids in straight channels micromachined in silicon" *Clin. Chem. 40(1):43–47.*

* cited by examiner

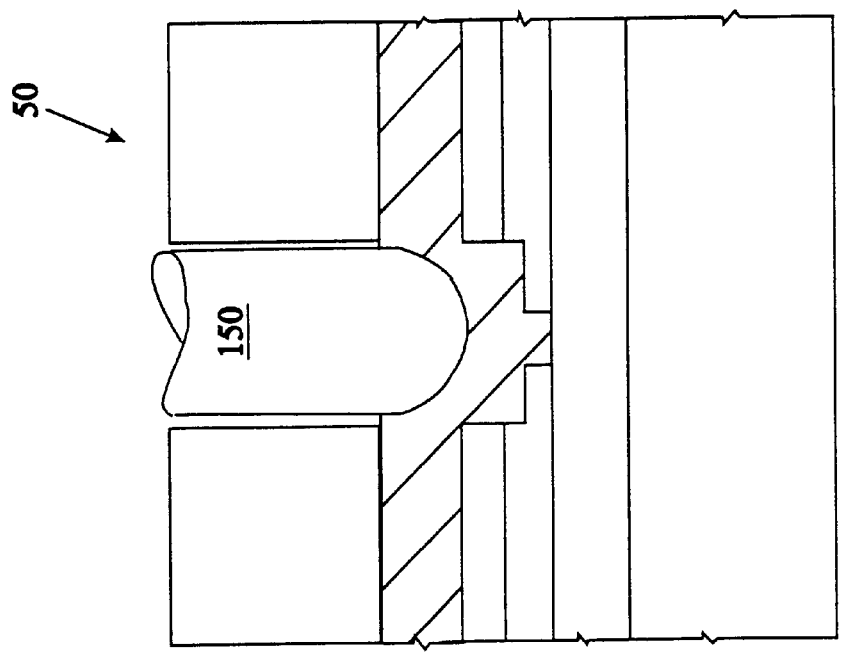
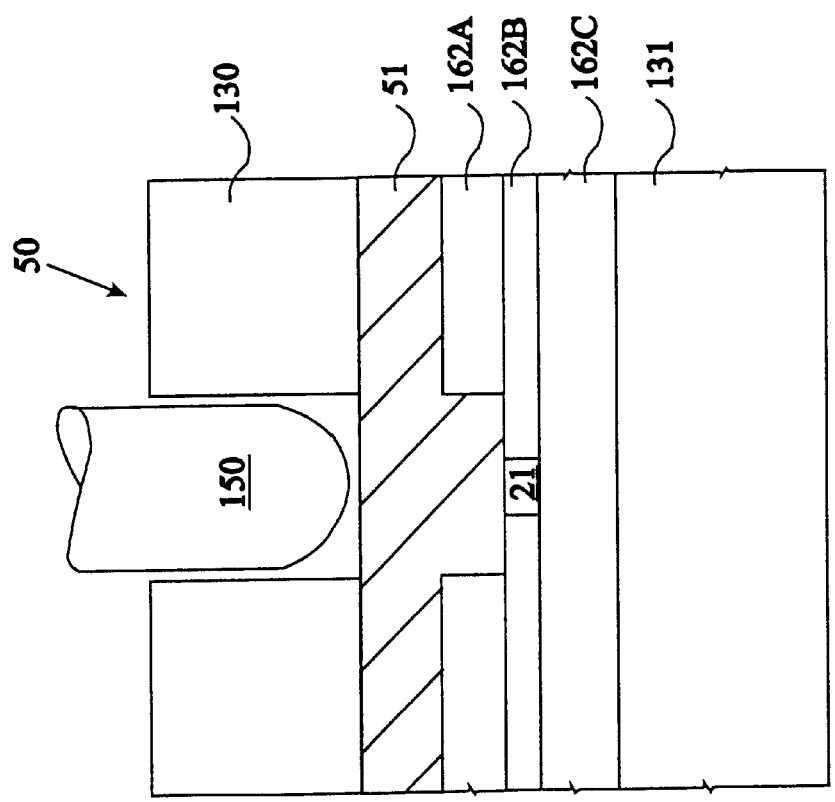
FIG. 4B
FIG. 4A

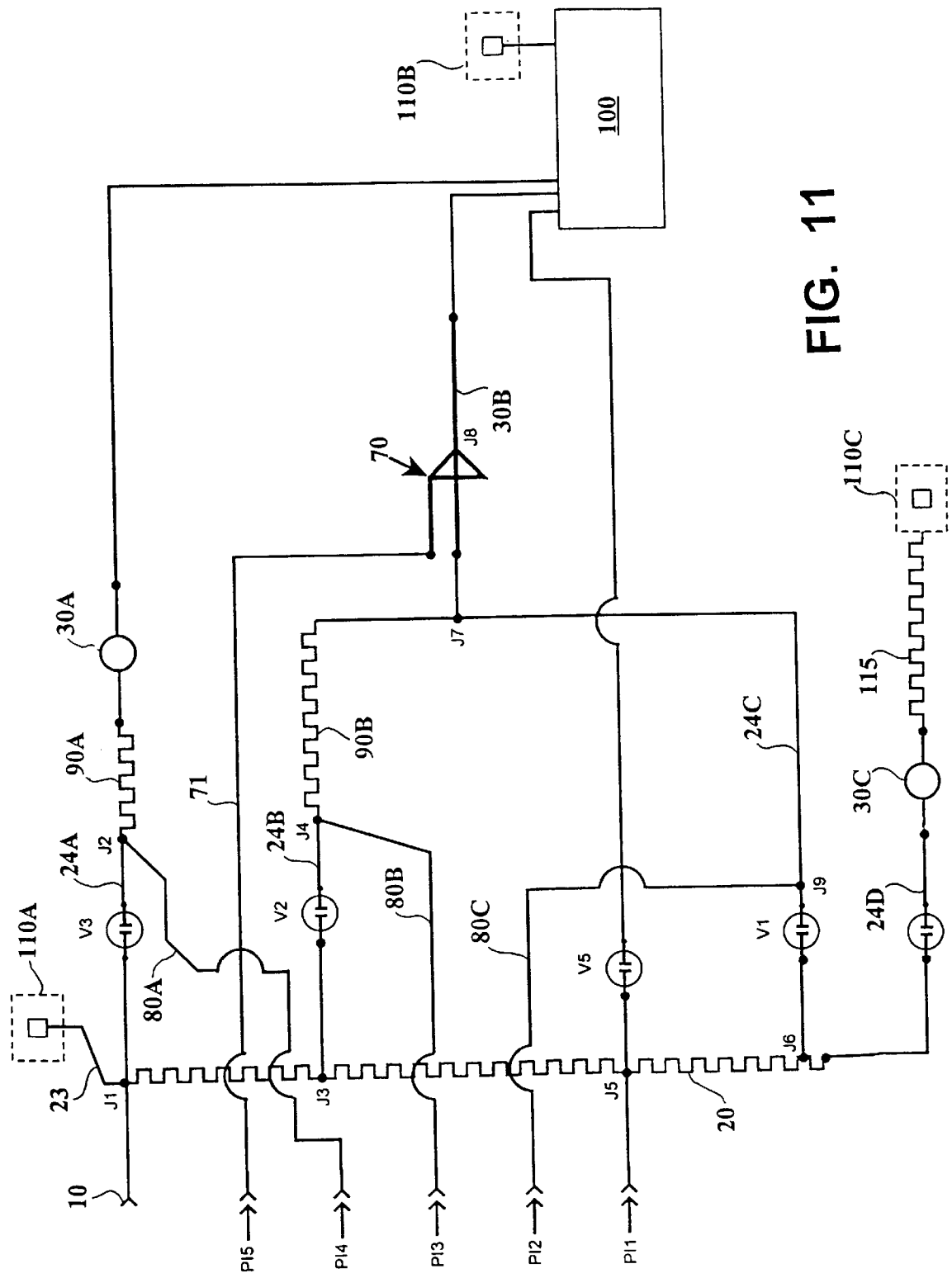

METHOD OF MAKING A LIQUID ANALYSIS CARTRIDGE

CROSS-REFERENCE TO RELATED APPLICATIONS

This application is a divisional of co-pending U.S. application Ser. No. 09/080,691 filed May 18, 1998 now abandoned.

FIELD OF THE INVENTION

This invention relates to microfluidic cartridges for analysis of liquid samples, and in particular to cartridges having a convoluted sample storage channel and to cartridges having a flow cytometric measuring region.

BACKGROUND OF THE INVENTION

With the advent of micro-machining technology, microfluidic devices have proliferated (for example, U.S. Pat. No. 5,637,469 to Wilding et al., U.S. Pat. No. 4,983,038 to Ohki et al., U.S. Pat. No. 4,963,498 to Hillman et al., U.S. Pat. No. 5,250,263 to Manz et al., U.S. Pat. No. 5,376,252 to Ekstrom et al., E.P. Patent Publication 0381501B1, and Petersen, E. (1982) *Proc. of the IEEE, vol.* 70, No. 5, pp. 420–457). A practical limitation for particle-containing liquids such as blood is the sedimentation of particles within the device. Following loading the liquid in the device, appreciable particle sedimentation can occur within the time required to position the device in a measurement apparatus. For example, if the sample flow is slowed or stopped, blood cells can measurably settle out of plasma within 20 seconds. Without a sample management method and apparatus for sedimentation mitigation, quantitative analysis, especially using more than one analysis method sequentially, is impractical. Moreover, if samples are first collected and then transported to a measurement apparatus, as in a clinical setting or in field sampling, particle sedimentation can make accurate analysis impossible.

Microfluidic devices having sample storage reservoirs are known in the art (for example, E.P. Patent Publication 0381501B1). Because of particle sedimentation, these devices are useful only for samples without particles. Flow cytometric microfluidic devices are also known in the art (for example, U.S. Pat. No. 4,983,038 to Ohki et al.). Flow cytometric measurements are specifically applicable to particle-containing liquids. However, without sedimentation mitigation the measurements can be performed only immediately following sample collection.

SUMMARY OF THE INVENTION

The present invention provides an apparatus and method for storing a particle-containing liquid. The storage apparatus comprises a fluidic convoluted flow channel having a plurality of particle capture regions therein. Particle capture regions are bends in the channel that provide local gravitational minima. When sample flow is arrested (i.e. stopped or slowed) during operation or storage, each of the particles sediments in the nearest particle capture region. Unlike a storage reservoir, the particles do not aggregate in a single clump. Because the particles are locally captured in a plurality of regions, it is possible to rapidly and effectively reconstitute the sample following sedimentation. The storage channel is preferably spatially periodic, where the term spatially periodic channel is used herein for a channel having a substantially constant number of particle capture regions per unit volume. Spatial periodicity facilitates sample reconstitution. The storage channel is more preferably an isotropic spatially periodic channel, where the term isotropic is used herein for a channel suitable for storing a particle-containing liquid regardless of channel orientation.

The particles can be resuspended by either a continuous or a reversing flow. For resuspension by continuous flow, the arrested sample flow is re-started and particles rejoin the sample fluid. The leading edge and trailing edge of the sample storage segments are discarded, but the middle segment is resuspended to a homogeneous mixture identical to the original sample. For the suspension by a reversing flow, a plurality of resuspension cycles are employed. Each resuspension cycle includes a dispense portion to sweep a volume of the stored sample, and an aspirate portion to sweep the volume in the opposite direction. Flow rates, swept volume and number of cycle are tailored to the sample fluid.

This invention further provides a fluidic analysis cartridge having a convoluted storage channel therein. The cartridge contains a sample inlet, a convoluted sample storage channel in fluidic connection with the inlet, an analysis channel, having an analysis region, in fluidic connection with the storage channel, and a valve interface positioned between the storage channel and the analysis region. The inlet includes an inlet shut-off interface to prevent leakage of the stored sample through the inlet. The cartridge further includes a resuspension pump interface to resuspend a sedimented sample by sweeping the sample from the storage channel in a continuous or reversing flow. The convoluted storage channel enables accurate analysis of particle-containing samples. The sample analysis region provides for detection by any means known in the art, for example optical, electrical, pressure sensitive, or flow sensitive detection. For electrical detection, the cartridge can include an electrical interconnect. For optical detection, the cartridge can include a window positioned over the analysis region. The optical analysis can employ optical absorption, fluorescence, luminescence or scattering. Particularly useful are absorption and flow cytometric analyses.

A plurality of analysis channels can be included in a single cartridge. The analysis channels can be joined to reagent inlets to mix the sample with reagents such as diluents, indicators and lysing agents. The reagents can be fed into the cartridge using a pump, for example a syringe pump. The reagent can alternatively be stored in a reservoir in the cartridge. For microscale channels, having laminar flow, mixing of the reagent with the sample is predominantly diffusional mixing. A mixing channel can be positioned between the reagent inlet and the analysis region to allow mixing and reaction of the reagent with the sample. The cartridge can include additional valves and pumps for flow management. The analysis cartridge can be a self-contained disposable cartridge having an integral waste storage container to seal biological and chemical waste. The storage container can include a vent to release gases during fluid loading. The cartridge can have alignment markings thereon to facilitate positioning in an analysis instrument.

This invention further provides a disposable fluidic hematology cartridge and a method for using the cartridge. The hematology cartridge has both an absorption measuring channel and a flow cytometric measuring channel. The cartridge can include a convoluted storage channel. It can further include reagent inlets, mixing channels, a waste storage container, and valves and pumps. The flow cytometric measuring channel preferably has a means for forcing particles in the sample fluid into single file. This can be accomplished with a constricted flow passage. It is preferably accomplished using a sheath flow assembly.

This invention further provides a sheath flow assembly. The sheath flow assembly includes a sample channel and first and second sheath fluid channels positioned on either side of and converging with the sample channel. The assembly also includes upper and lower sheath fluid chambers positioned above and below and converging with the sample channel. The sheath fluid channels provide hydrodynamic focusing in the widthwise direction, and the sheath fluid chambers provide hydrodynamic focusing in the depthwise direction. Because the assembly provides hydrodynamic focusing, geometric focusing is not required. It is not necessary for the sample channel to contract in either the widthwise or depthwise direction. Contracting channels can also be employed.

A sample analysis instrument for use with a fluidic analysis cartridge is further provided. The instrument includes a cartridge holder, a flow cytometric measuring apparatus positioned for optical coupling with a flow cytometric measuring region on the cartridge, and a second measuring apparatus positioned to be coupled with a second analysis region on the cartridge. The cartridge holder can include alignment markings to mate with cartridge alignment markings. It can also include pump mechanisms to couple with pump interfaces on the cartridge and valve mechanisms to couple with valve interfaces on the cartridge.

The convoluted storage channel provides one means for resuspending particles sedimented during sample storage. This invention also provides analysis cartridges having a storage reservoir and an alternative resuspension means. The resuspension means can be an ultrasonic vibrator acoustically coupled to the reservoir or a mechanical agitator either positioned within the reservoir or mechanically coupled to the reservoir.

The flow cartridges of this invention can be formed by any of the techniques known in the art, including molding, machining and etching. They can be made of materials such as metal, silicon, plastics and polymers. They can be formed from a single sheet, from two sheets, or, in a preferred embodiment, from a plurality of laminated sheets. This invention further provides a method of fabricating a laminated fluidic flow channel. In the method, flow elements are formed in rigid sheets and abutting surfaces of the sheets are bonded together. The term rigid sheet is used herein for a substantially inelastic sheet. A rigid material still exhibits flexibility when produced in thin sheets. The flow elements can include fluid channels within the plane of the sheet, vias (holes) to route the fluid to the next layer, analysis regions, pump interfaces and valve interfaces. The flow elements can be formed by methods including machining, such as die cutting or laser ablating, and molding. The sheets can be bonded together by the use of an adhesive or by welding. They can alternatively be held together with mechanical compression.

BRIEF DESCRIPTION OF THE DRAWING

FIG. 1, comprising

FIG. 2, comprising

FIG. 3, comprising

FIG. 4, comprising FIGS. 4A–B, is a pinch valve (A) unactuated and (B) actuated.

FIG. 7, comprising

FIG. 10, comprising

FIG. 11 is a schematic drawing of an analysis cartridge having a convoluted storage channel and a plurality of mixing and analysis channels.

FIG. 13, comprising

DETAILED DESCRIPTION OF THE INVENTION

Figure 1A:
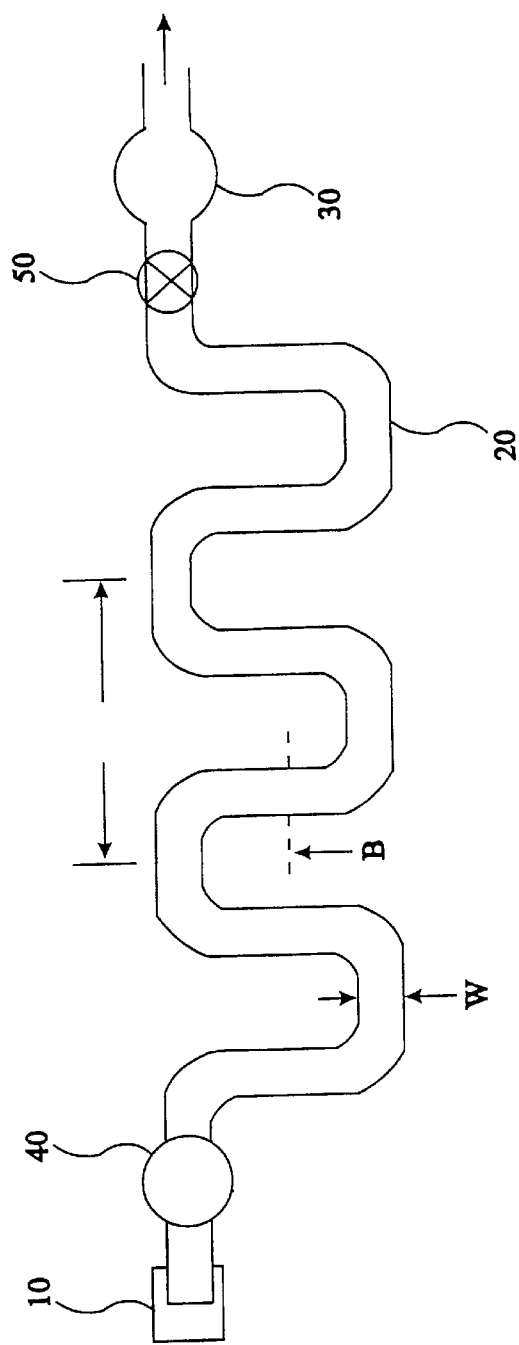
FIGS. 1A–B, is an analysis cartridge with a convoluted storage channel in (A) plan view and (B) cross section.

This invention is further illustrated by the following preferred embodiments. In the drawings, like numbers refer to like features, and the same number appearing in more than one drawing refers to the same feature. The members of the flow systems of this invention are fluidically connected. The term "between" refers to the fluidic positioning, which does not necessarily correspond to the geometric positioning. The terms "top", "bottom" and "side" refer to the orientation in the drawings, which is not necessarily the orientation of the members in operation.

Figure 1B:
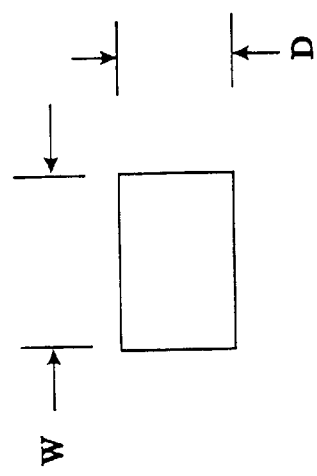

FIG. 1 shows the flow system contained within the cartridge of this invention. The term cartridge is used herein for a fluidic device which is preferably, but not necessarily, disposable and which can be coupled with measurement, pumping, electronic, fluidic or other apparatus. It includes sample inlet 10, convoluted sample storage channel 20, resuspension pump interface 40, sample analysis region 30 and valve interface 50. The flow system is preferably a microfluidic flow system. The term microfluidic channel is used herein for fluid elements dimensioned so that flow therein is substantially laminar. In a laminar flow system turbulence is negligible. To maintain laminar flow in the storage channel, preferably the width of the channel is less than 2000 $\mu$m and the depth of the channel is less than 300 $\mu$m. To prevent clogging by particles, the dimension must be greater than the largest particle dimension, typically greater than 25 $\mu$m.

The sample inlet has an inlet shut-off interface to prevent the loaded sample from leaking out of the cartridge. In the illustrated embodiment the sample inlet comprises a septum. A hypodermic needle is used to inject the sample through the septum. Upon removal of the needle, the septum forms a shut-off to keep the sample in the flow system. Alternatively, the sample inlet can be a non-sealing inlet such as a capillary or a channel which mates with a sample conduit. If the inlet does not have an integral shut-off interface, it can be combined with a separate valve interface.

The resuspension pump interface is used for reconstituting a sedimented sample following stop flow or storage. The pump can provide continuous or reversible flow. For continuous flow resuspension, the leading edge and trailing edge of the sample storage segment must be discarded, but the sample segment in the middle is resuspended to a homogeneous mixture identical to the original sample. Significant operating parameters are the resuspension flow rate and the resuspension time. Reversible flow resuspension uses a plurality of dispense/aspirate cycles. In this protocol, in each cycle the sedimented sample is swept through the channel in dispense mode and then swept back in aspirate mode. The swept volume is typically 1–4 periods of the spatially periodic channel. The aspirated volume is typically equal to the dispensed volume. The significant operating parameters are the resuspend swept volume, the number of resuspension cycles and the resuspension flow rate. For either protocol, the resuspension parameters are specific to the particle laden fluid under consideration and the geometry of the storage channel. Suitable resuspension flow rates and times can be calculated or determined empirically.

To calculate the required flow rate, $\dot{V}$, the channel geometry and fluid properties are considered. For substantially rectangular geometries, the critical flow rate is a function of the width W and depth D of the channel and of the effective viscosity $\mu_{eff}$ of the particulate suspension according to:

$$\dot{V} = \frac{2D^2 W \tau_{crit}}{3\mu_{eff}} \qquad \text{Equation 1}$$

By extrapolation of the data in Alonso et al. (1989), Biorheology 26, 229–246, the critical wall shear stress, $\tau_{crit}$, for cell suspension maintenance is estimated to be 0.14 Pa. As shown by Eq. 1, for greater channel dimensions the critical flow rate is greater. For a channel 50 $\mu$m×100 $\mu$m in cross-section, the critical flow rate is 0.008 $\mu$l/s. For a 300 $\mu$m×1000 $\mu$m channel, the critical flow rate is 2.8 $\mu$l/s.

The valves and pumps of this invention can be entirely incorporated in the cartridge, or the cartridge can include only valve and pump interfaces, and the remainder of the valve and pump mechanisms can be external to the cartridge. A pump (valve) comprises a pump (valve) interface and a pump (valve) mechanism. The interface is that portion which is directly connected to flow elements, and the mechanism is the exterior portion. The cartridge can be inserted in measurement apparatus comprising valve and pump mechanisms. Upon loading the cartridge in the apparatus, the valve and pump mechanisms engage the valve and pump interfaces. The valves can be either normally open or normally closed. They can be manually or automatically actuated.

Sedimentation in convoluted storage channels is illustrated in FIG. 2. When the flow is arrested the particles sediment in the nearest particle capture region, which are bends at gravitational potential minima. The gravity vector is illustrated in the drawings. The channels contain a plurality of particle capture regions so that the particles cannot aggregate in a single clump. The illustrated convoluted channels are spatially periodic. The term spatially periodic channel is used herein for a channel having a substantially constant number of particle capture regions per unit volume. This facilitates recreating a homogeneous sample upon resuspension. The illustrated embodiments are spatially periodic in a conventional geometric sense, having repeating units of length $\lambda$. Alternatively, the channel can be randomly convoluted but nonetheless have a substantially constant number of particle capture regions per unit volume.

Figure 2A:
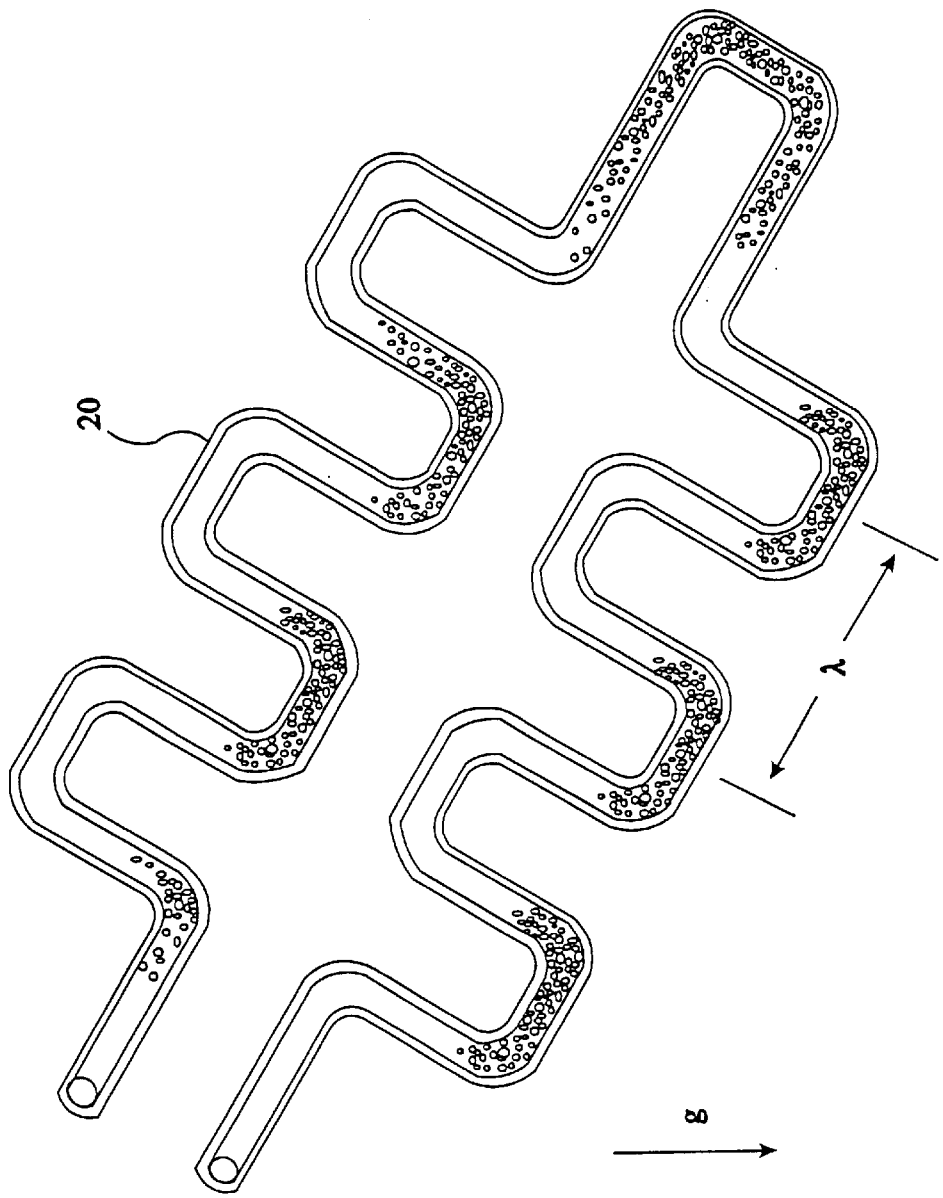
FIGS. 2A–B, shows convoluted storage channels with particle sedimentation for (A) an anisotropic storage channel and (B) an isotropic storage channel.

The channel of FIG. 2A is suitable for storing particle-containing liquid in the illustrated orientation. If it were aligned along the channel axis, i.e. rotated so that the inlet and outlet were at the top, all of the particles would accumulate in the bottom capture region and would be difficult to resuspend uniformly. This type of spatially periodic channel is referred to herein as anisotropic because the suitability for storage depends on orientation. This anisotrophy can be disadvantageous. To prevent clumping the cartridge must be carefully handled to ensure that it is never aligned along the channel axis.

Figure 2B:
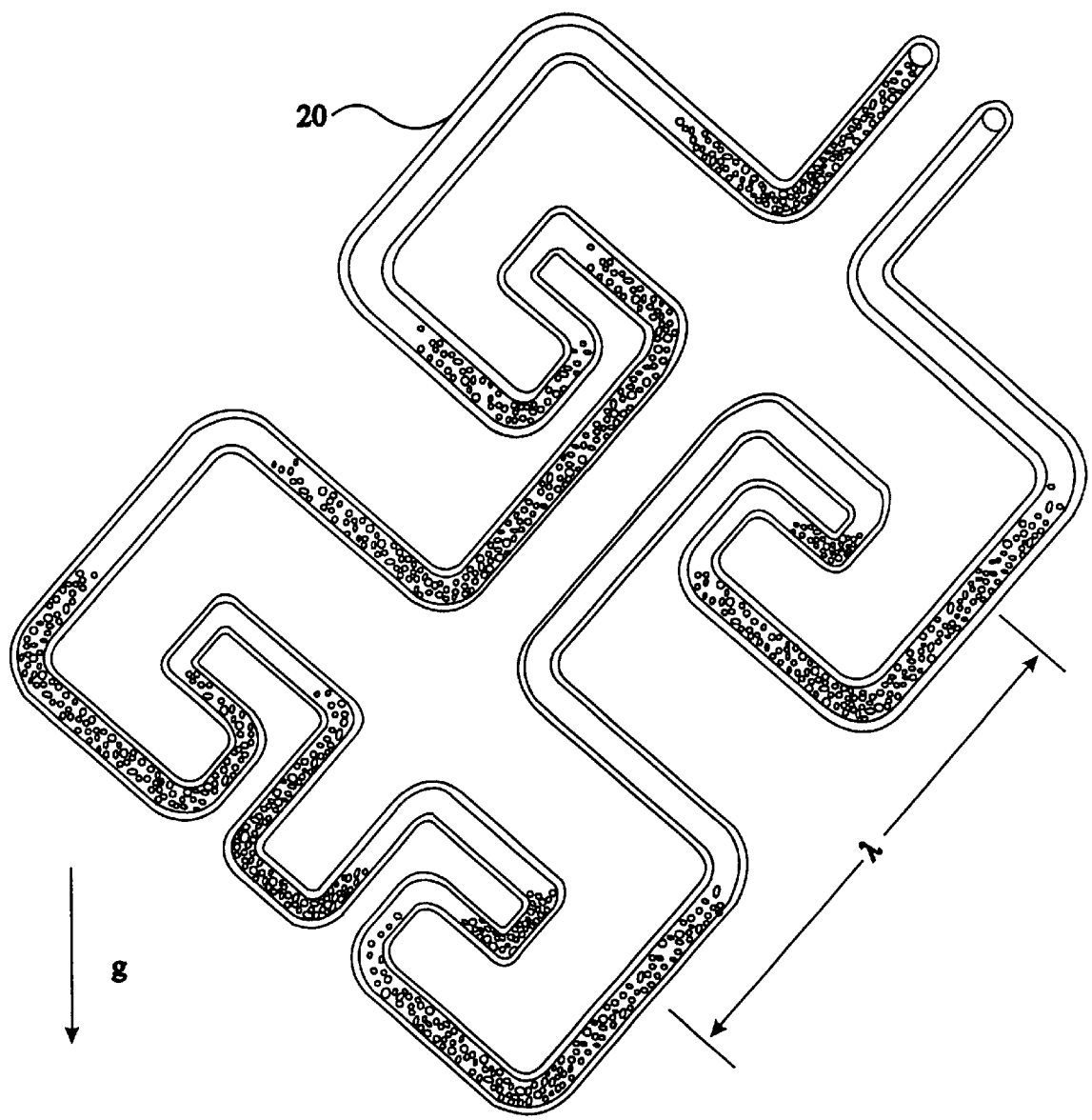
Figure 3A:
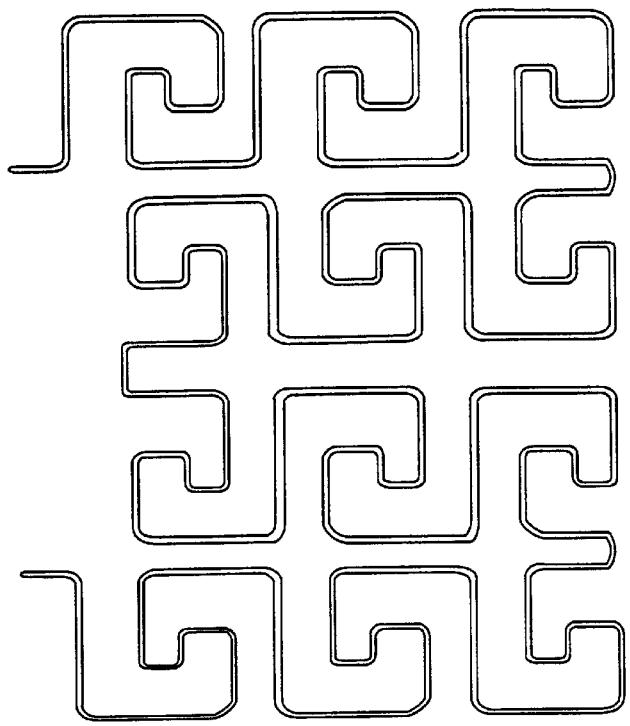
FIGS. 3A–D, are isotropic spatially periodic channels.
Figure 3B:
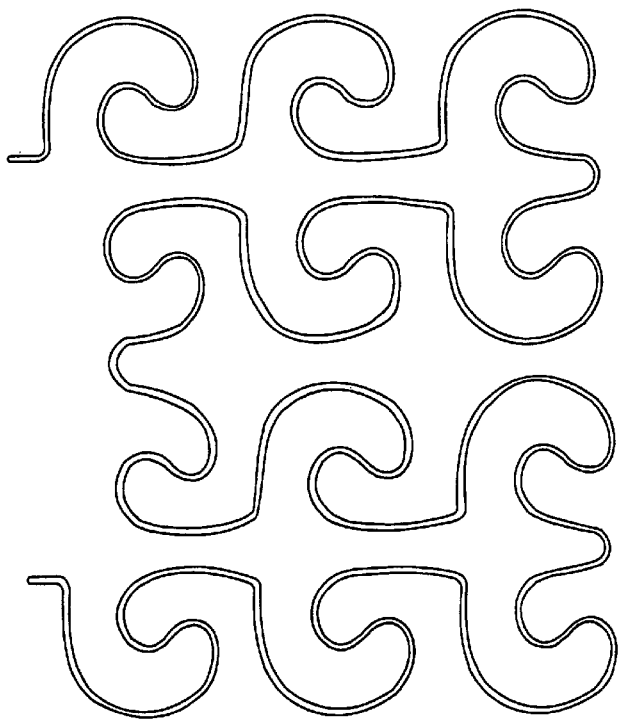
Figure 3C:
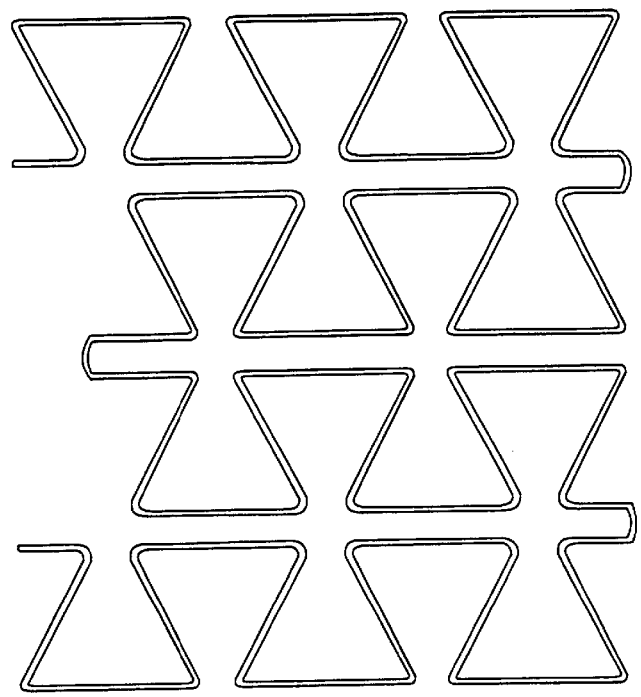
Figure 3D:
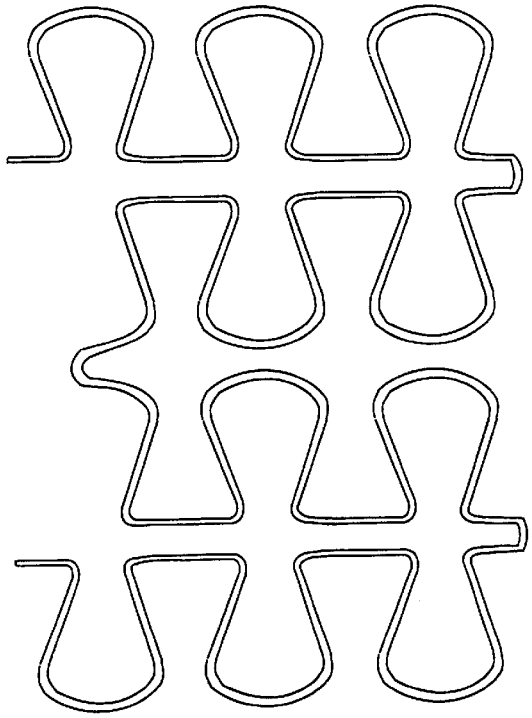

The channel of FIG. 2B can be used for storage at any orientation and is thus referred to herein as an isotropic storage channel. Isotropic channels are preferred because it is not necessary to maintain a particular orientation during handling. Further examples of isotropic spatially periodic channels are shown in FIG. 3. The channel of FIG. 3A has the same structure as the channel of FIG. 2B but with more repeated units. The channel of FIG. 3B is similar but with rounded corners. This can be advantageous for manufacturing and assembly. The channels of FIGS. 3C and D are referred to as "omega" channels, angular in FIG. 3C and rounded in FIG. 3D. Omega channels are similar to the square wave channel of FIG. 2A except that bringing the bases of the square wave toward one another adds additional capture regions, and thereby makes the channel isotropic. FIG. 3 shows a few examples of storage channels; numerous other isotropic spatially periodic channels can be utilized. In the following schematic drawings square waves are used as a generic illustration of convoluted channels. Other embodiments may be preferred and in particular isotropic channels may be preferred.

This invention also provides a structure containing an isotropic storage channel. The structure is any solid material with a channel formed therein. The structure can be a disposable cartridge or a permanently installed element of a measurement or reaction instrument. It can be a microscale channel dimensioned for laminar flow or a macroscale channel dimensioned for turbulent flow. One embodiment is a bioreactor wherein reagents, which can include cells, are incubated in the channel followed by resuspension of particles.

A preferred embodiment of valve interface 50 is shown in FIG. 4. FIG. 4A shows a cross-section of the valve in the open position and FIG. 4B shows the valve in the closed position. Channel 21, running orthogonal to the plane of the paper, has walls formed by sheet 162B, and top and bottom formed by sheets 162A and C. Elastic seal 51 fits within an opening in sheet 162A. The fluid element containing sheets are sandwiched between upper cartridge case 130 and lower cartridge case 131. The valve mechanism includes valve pin 150 which is made of a rigid material, for example metal or plastic. The valve pin is guided by an opening in upper case 130. When actuated, the pin presses against seal 51, which extrudes into the channel, thereby closing it. Note that although it is termed a pinch valve, the channel itself is not pinched closed. The valve mechanism can be incorporated into the cartridge or it can be a separate element. Seal 51 is made of a deformable material such as silicone, urethane, natural rubber or other elastomers. In the illustrated embodiment, the channel is formed with three separate sheets, 162 A–C; it can instead be formed in fewer than or in more than three sheets. The pinch valve of FIG. 4 is an example of a valve that can be used with the analysis cartridge. Other valves can instead be used.

Figure 5:
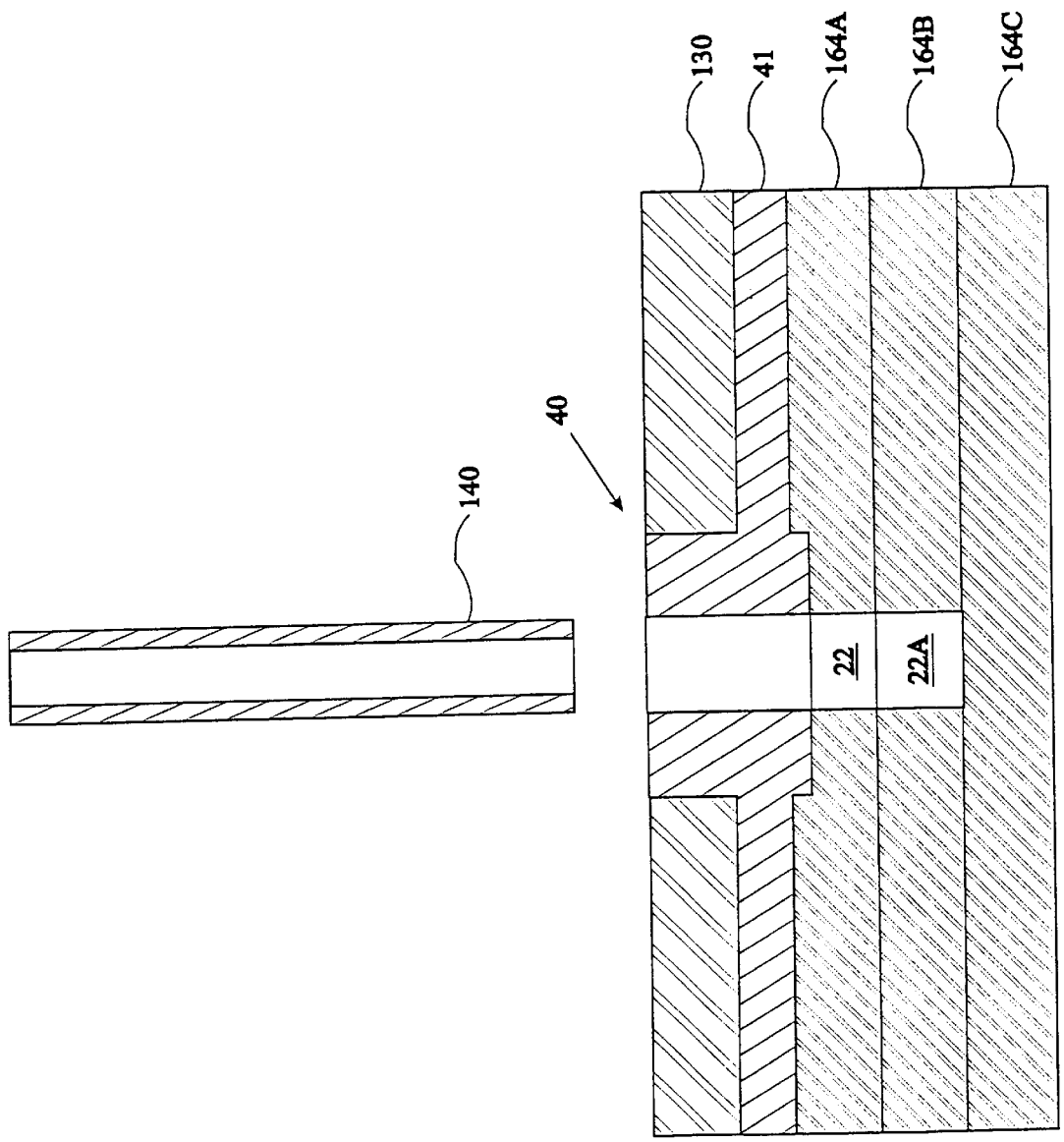
FIG. 5 is a syringe pump interface.

An embodiment of resuspension pump interface 40 is shown in cross-section in FIG. 5. Channel 22A, running orthogonal to the plane of the paper, has walls formed within sheet 164B and bottom formed by sheet 164C. Fluid communication via 22 is a circular hole in sheet 164A allowing fluid flow from 140 to 22A. Elastic seal 41 fits between sheet 164A and upper cartridge case 130. The pump mechanism includes cannula 140, which is preferably connected to a syringe pump, not shown. The cannula can be inserted into seal 41 to introduce fluids into channel 22A. The cannula can be essentially a needle with a polished tip to avoid damaging the seal. In the resuspension procedure, a fluid such as saline or water is it injected into the channel through the cannula, and it sweeps the sample fluid through the channel. To reverse the flow, the saline in extracted through the cannula. The syringe pump interface can be used both as a pump, one- or two-directional, and as a reagent inlet. The entire pump, interface and mechanism, can be incorporated in the cartridge, or only the interface can be incorporated and the mechanism can be separate.

The sample analysis region provides for detection by any means known in the art, for example optical, electrical, pressure sensitive, or flow sensitive detection. More then one analysis means can be employed in a single analysis region, for example optical and electrical. For electrical detection, the cartridge can include an electrical interconnect. The cartridge can be electrically connected to electrical measuring apparatus. For optical detection, the cartridge can include a window positioned over the analysis region for optical coupling with measuring apparatus such as light sources and photodetectors. The windows can be inserted glass or, if the channel is formed in transparent sheets, the sheets themselves can serve as windows. The optical detection can be absorption, luminescent, fluorescent or scattering based. The cartridge can comprise a plurality of sample analysis regions. One of the analysis regions can provide a filling status gauge to indicate that the storage channel is filled. The gauge can be based on optical absorption measurement, pressure measurement, conductivity measurement, flow measurement or any measurement that indicates the presence of a fluid in the gauge. For absorption measurement, visual observation of filling status may be used.

Figure 6:
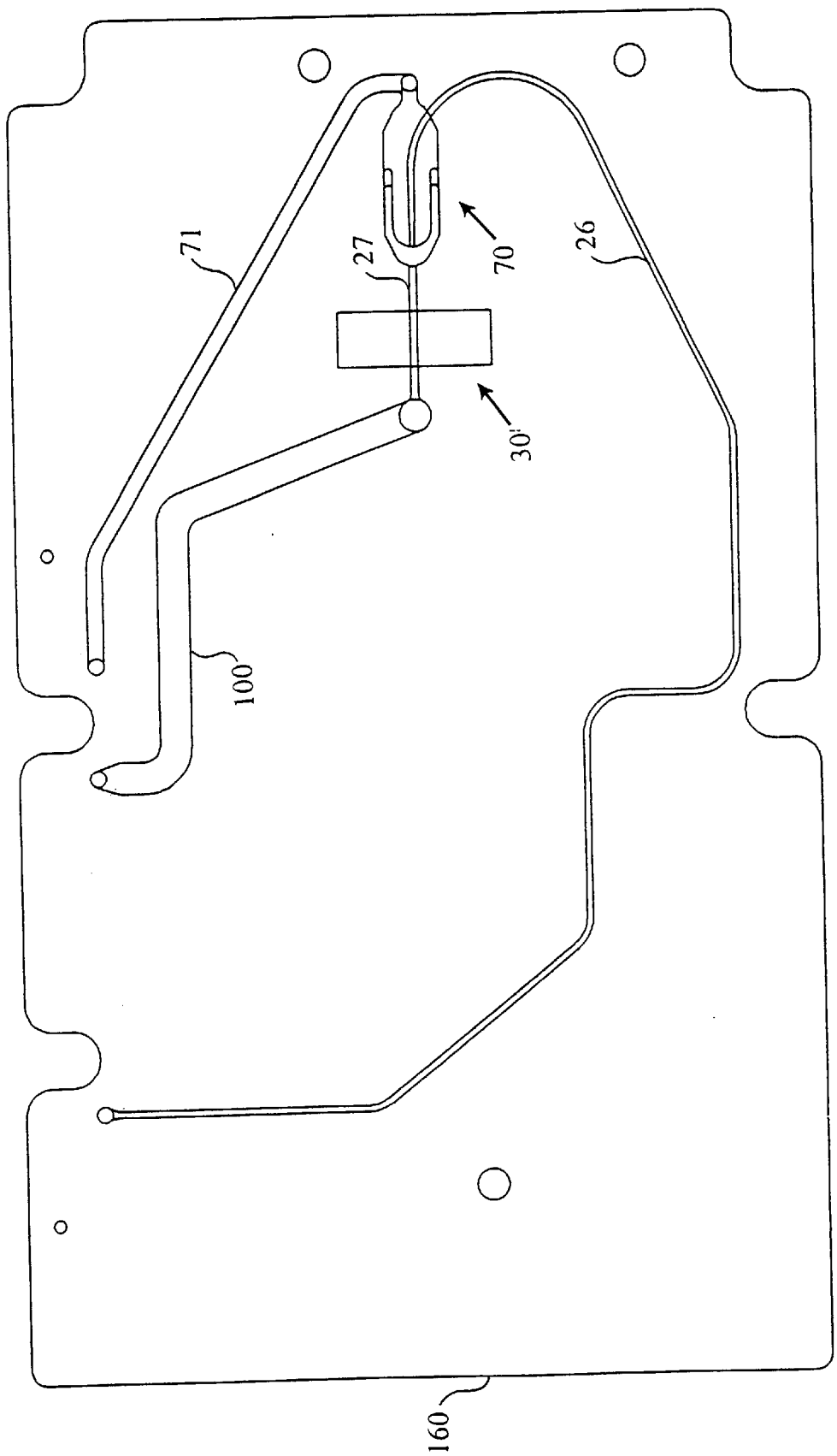
FIG. 6 is a plan view of a sheath flow assembly.
Figure 7A:
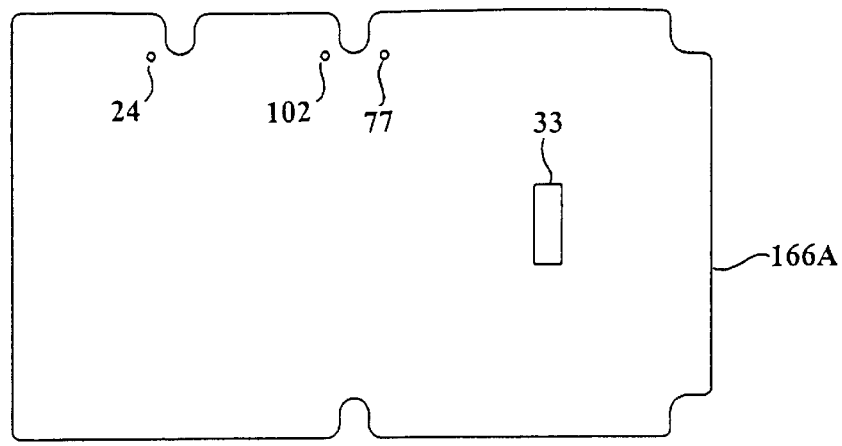
FIGS. 7A–G, shows the individual sheets which are laminated together to form the sheath flow assembly of FIG. 6.
Figure 7B:
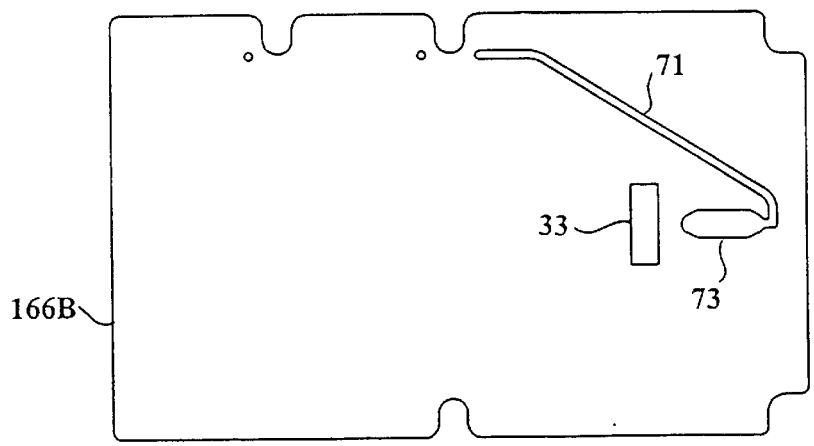
Figure 7C:
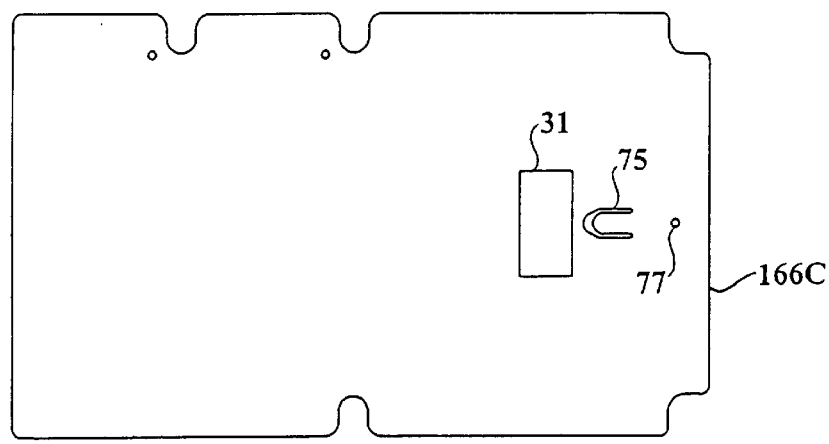
Figure 7E:
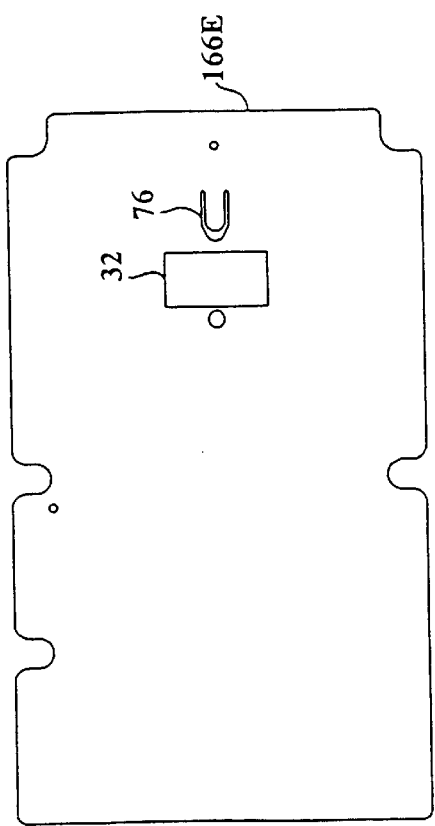
Figure 7G:
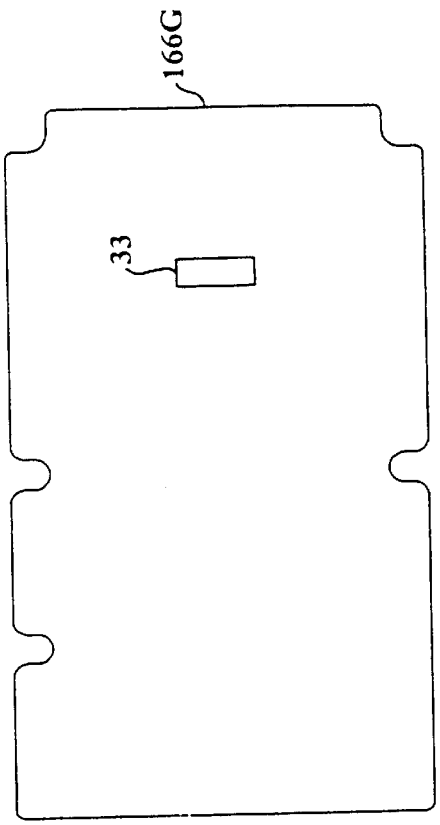
Figure 7D:
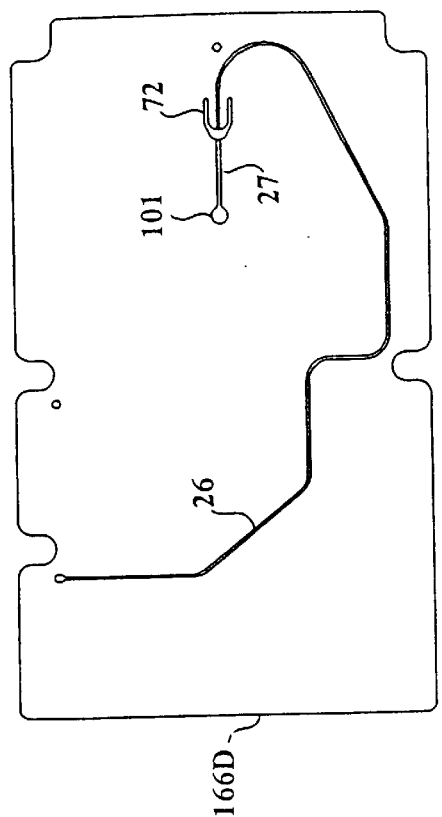
Figure 7F:
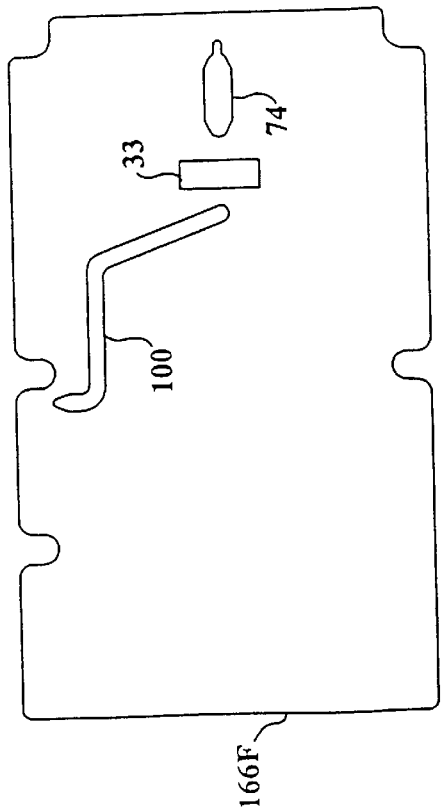

In a preferred embodiment, the analysis region is a flow cytometric analysis region. Preferably a sheath flow assembly is positioned along the analysis channel before the flow cytometric analysis region. FIGS. 6 and 7 illustrated a preferred embodiment of the sheath flow assembly. The assembly comprises seven sheets, 166A–G, which are laminated together to form the fluidic elements of analysis cartridge 160. The analysis channel, comprising core stream channel 26 and sheathed stream channel 27, is connected to the convoluted storage channel (not shown). In sheath flow assembly 70, first and second sheath fluid channels, jointly labeled as element 72 (FIG. 7D), are positioned on either side of and converge with channel 26. In this embodiment the diameter of the sheathed portion is greater than the core portion of the analysis channel. The sheath fluid channels extend into layers 166C and E, and are labeled as elements 75 and 76. The sheath fluid channels provide hydrodynamic focusing of particles in channel 27 in the widthwise direction. Upper and lower sheath fluid chambers 73 and 74 are formed in sheets 166B and F. When assembled, they are positioned above and below and converge with channel 26. The sheath fluid chambers provide hydrodynamic focusing in the depthwise direction. To minimize layer to layer depthwise discontinuities in the region where the sheath fluid channels and chambers converge with the analysis channel, the downstream edges are staggered. The edge of channels 75 and 76 are slightly to the right of the edge of channel 72. Sheath fluid is conducted to the sheath flow assembly through sheath fluid channel 71 (FIG. 7B). Vias 77 in sheets 166C–E connect channel 71 with the sheath fluid chambers. The sheath fluid chambers communicate fluid to the sheath fluid channels. In typical hydrodynamic focusing operation, the ratio of sheath flow to core stream 26 flow is around 130:1.

Following hydrodynamic focusing, flow cytometric measuring is performed in analysis region 30. The analysis region includes window recesses 31 and 32 in sheets 166C and E positioned above and below the focused sample. The window recesses accommodate glass inserts. In lieu of recesses, sheets 166C and E can themselves serve as windows. In the remaining sheets, optical clearing holes 33 allow optical access to the analysis region. The sheets in FIG. 7 are sandwiched between an upper case and a lower case. Layers 166A and G can be incorporated in the case. The illustrated embodiment also includes waste storage container 100. It is connected with flow channel 27 through vias 101 and to a case mounted storage container through vias 102.

One embodiment of the sheath flow assembly has been illustrated. Other sheath flow assemblies known in the art can be utilized, for example U.S. Pat. No. 4,983,038. Because this sheath flow assembly of the present invention provides both widthwise and depthwise hydrodynamic focusing, geometric focusing is not required. Although not necessary, the analysis channel can decrease in width and/or depth and in a downstream direction. Two-dimensional hydrodynamic focusing can also be achieved using the device of U.S. patent application Ser. No. 08/823,747, filed Mar. 26, 1997. In lieu of hydrodynamic focusing the flow channel can be constricted in the analysis region to provide single file particles, as described in single file, as described in U.S. Pat. No. 5,726,751.

Another preferred embodiment of the sample analysis region is an absorption analysis region. For increased sensitivity using an absorbance based assay the optical pathlength, i.e. the channel depth, in the absorption measurement region is increased. For decreased sensitivity to factors such as intermittent sample stream perturbations, optical window quality and optical measurement apparatus lens defects, the effective illumination area of the detection region can be increased by increasing the channel width. There is a design trade-off between increasing the channel width and depth and minimizing the volume of the microfluidic system. This balance can be determined for a specific assay, a specific set of light sources, detectors and optics, and the required accuracy and resolution.

Figure 8:
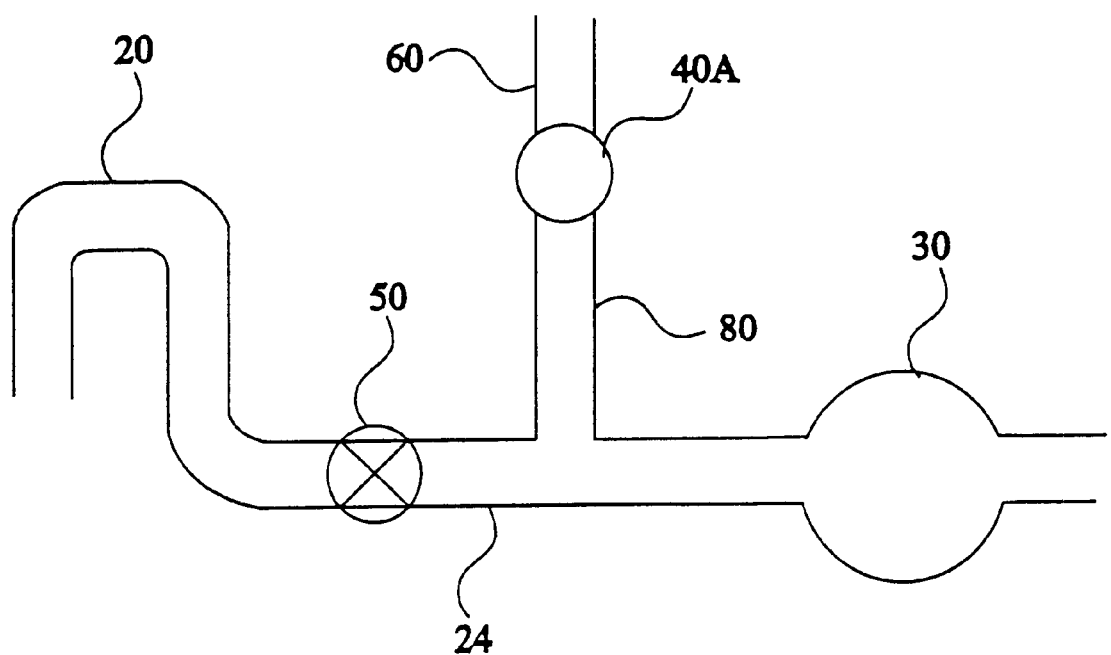
FIG. 8 shows a reagent channel joining the sample channel.

The cartridge can also include an inlet for mixing a reagent with the sample fluid prior to sample analysis, as shown in FIG. 8. The term "reagent" refers to any fluid that joins the sample fluid. It can be, for example, a diluent, a lysing agent, an indicator dye, a fluorescent compound, a fluorescent standard bead for flow cytometric calibration, or a reporter bead for flow cytometric measurement (U.S. Pat. No. 5,747,349). Between storage channel 20 and analysis region 30, reagent channel 80 joins analysis channel 24. The reagent channel is connected to pump interface 40A and reagent inlet 60. In a preferred embodiment the pump and the inlet are combined in a syringe pump. The cartridge includes valve interface 50 to separate the storage channel from the reagent inlet.

Figure 9:
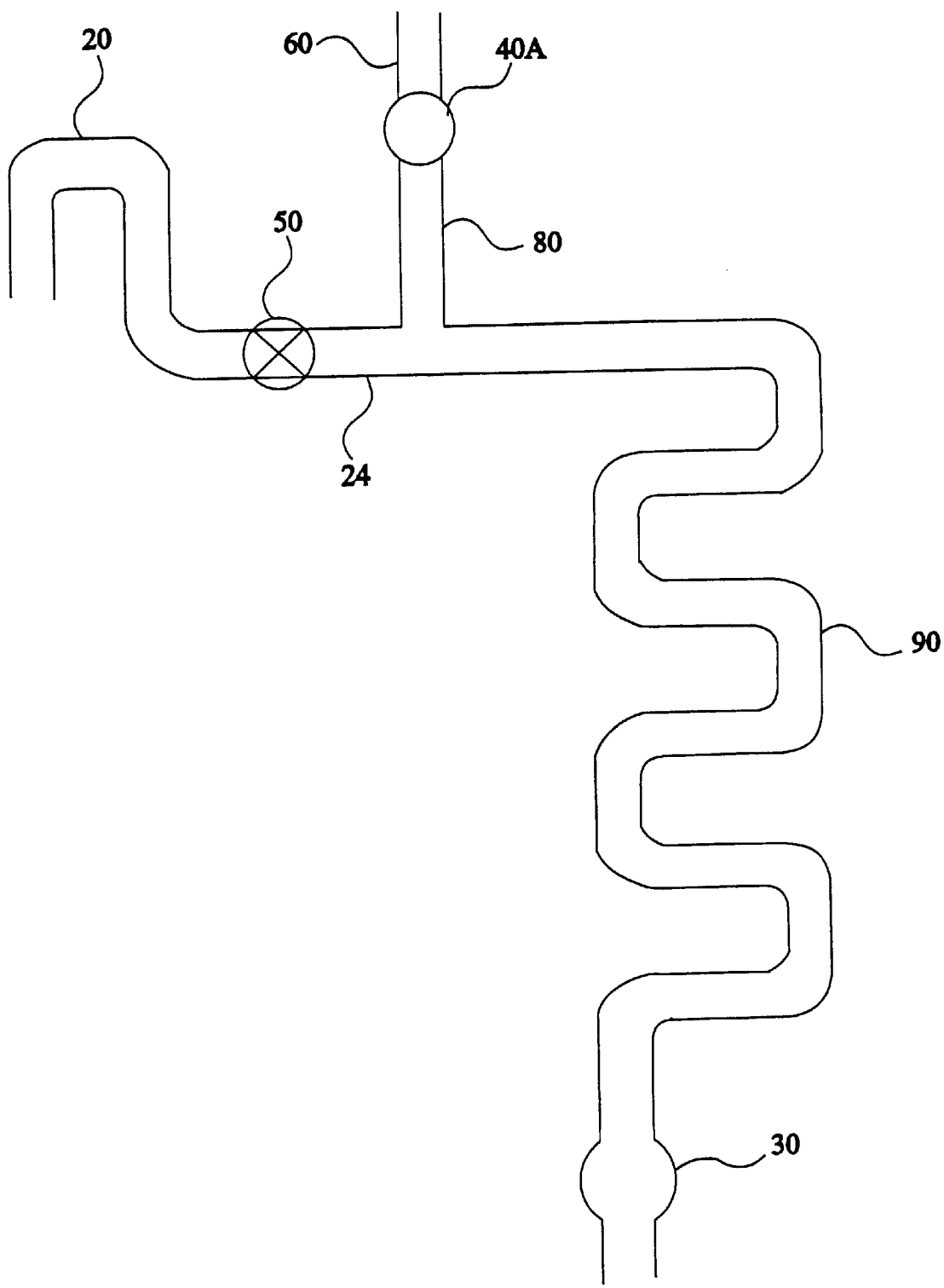
FIG. 9 shows a convoluted mixing channel following the junction of a reagent channel with the sample channel.

When the flow channels are microchannels having laminar flow therein, mixing between the reagent and the sample is predominantly diffusional mixing. The streams can join in side-by-side flow, as described in U.S. Pat. No. 5,716,852 and U.S. Ser. No. 08/829,679 filed Mar. 31, 1997, or in a layered flow for more rapid mixing, as described in U.S. Pat. No. 5,972,718 issued Oct. 26, 1999, and U.S. Ser. No. 08/938,585 filed Sep. 26, 1997. In order to allow for mixing and reaction prior to analysis, a mixing channel can be included, as shown in FIG. 9. Mixing channel 90 is positioned between the reagent inlet and the analysis region. The geometry of mixing channel 90 is selected to allow mixing and reaction between the sample and reagent streams. The mixing channel can be convoluted in order to achieve the desired time delay within a compact space. Alternatively, active mixing methods can be employed, including ultrasonic, mechanical, sonic, flow induced, etc.

Figure 10A:
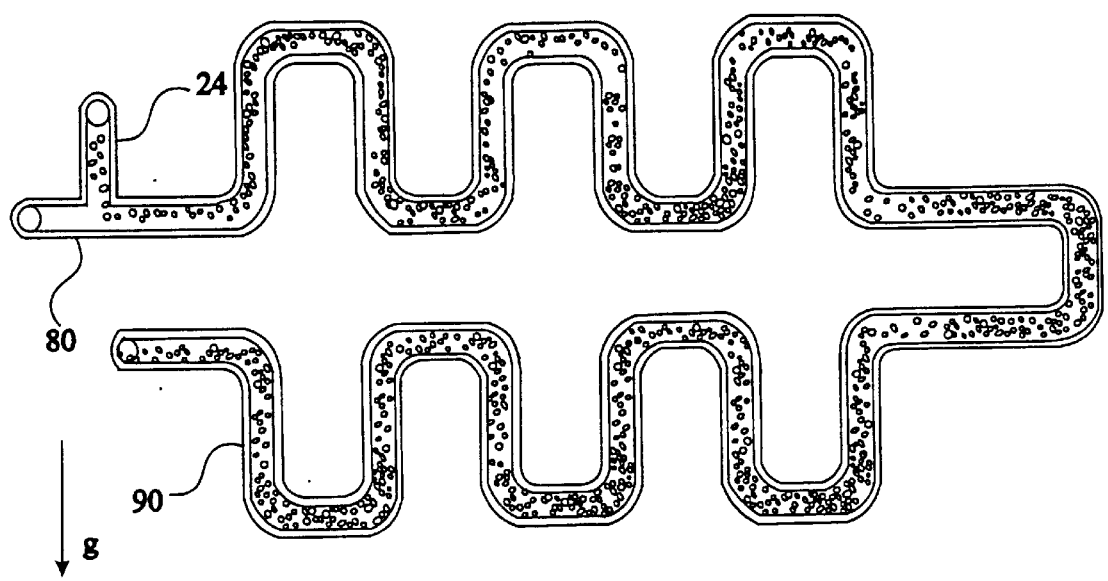
FIGS. 10A–B, illustrates mixing of a particle-containing sample with a reagent in (A) an anisotropic mixing channel and (B) an isotropic mixing channel.
Figure 10B:
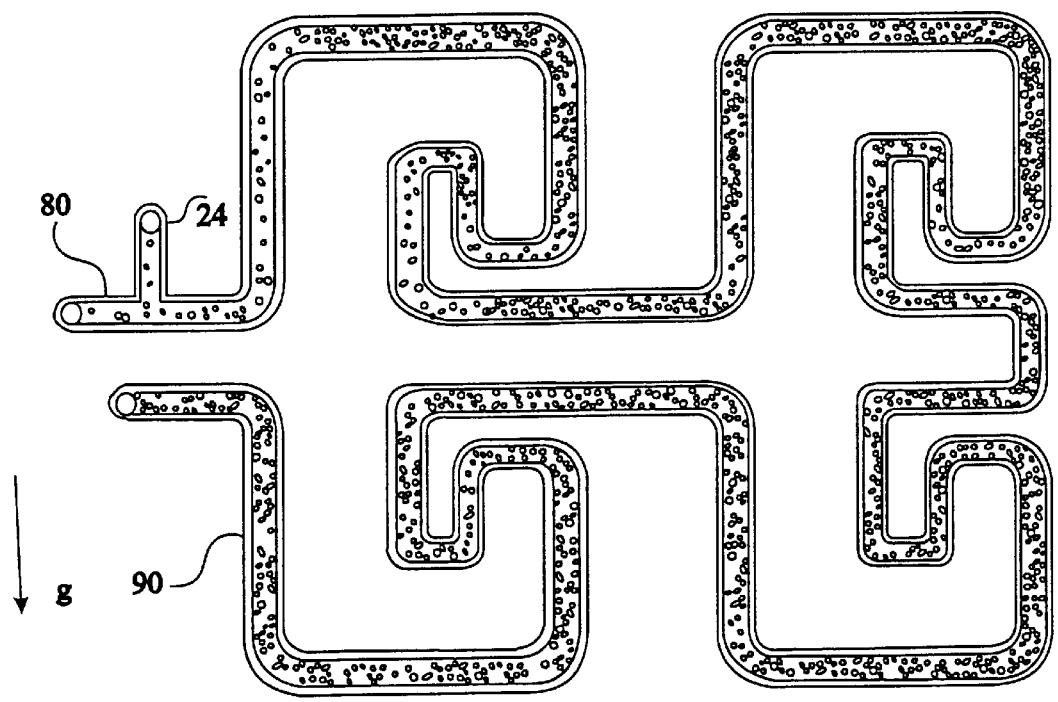

In the embodiment of FIG. 9 the mixing channel is illustrated as a square wave. For a particle-containing sample, it may be desired to allow diffusional mixing between smaller species within the sample and reagent streams without allowing particles in the sample screen to gravitationally settle into the reagent stream. FIG. 10 shows the effect of channel geometry on gravitational mixing. A square wave channel is illustrated in FIG. 10A. The particle-containing sample stream enters mixing channel 90 through channel 24 and reagent stream enters through channel 80. In the upper half of the mixing channel the sample stream is gravitationally above the reagent stream and particles tend to settle into the reagent stream. In the lower half of the mixing channel this is reversed and particles settle back into the sample stream. This reversal of top and bottom for the sample stream and reagent stream can be used more effectively in an isotropic channel as illustrated in FIG. 10B. In a spatially periodic isotropic channel the gravitational top and bottom of the channel interchange within each repeating unit. This counteracts the effect of gravity on the particles in the sample stream. The isotropic spatially periodic channel is therefore useful for sedimentation mitigation as well as sedimentation resuspension.

The cartridge can provide for more than one analysis region, in series or in parallel. Multiple parallel analysis regions are illustrated schematically in FIG. 11. The device of FIG. 11 comprises sample inlet 10, storage channel 20, resuspension pump interface PI1 (Pump Interface 1), and analysis regions 30A–C. At junctions J1, J3, J5, J6 and at the end of the storage channel, fluid from the sample storage channel can be directed to analysis channels 24A–D and to waste storage container 100. Note that in this embodiment the resuspension pump is fluidically connected to the storage channel in the middle of the channel rather than at the beginning of the channel 1. Preferably the sample segment between J1 and J3 flows through valve V3 for analysis, the sample segment between J3 and J5 flows through valve V2 for analysis and the segment between J5 and J6 flows through valve V1 for analysis.

The cartridge further includes pump interfaces PI2–PI5, valve interfaces V1–V5, reagent channels 80A–C, sheath flow assembly 70, waste storage container 100, and vents 110A–C. In a preferred embodiment, the sample inlet is a septum, the pump interfaces are syringe pump interfaces and the valve interfaces are pinch valve interfaces. The vents are made of gas permeable plugs having a reduced permeability when wet. The storage and mixing channels are illustrated as square waves but are preferably isotropic spatially periodic channels. The sheath flow assembly is preferably as illustrated in FIGS. 6 and 7. Analysis region 30C is a filling status gauge providing visual indication of proper sample load. Analysis region 30A is an absorption measurement region, optically coupled with measurement apparatus comprising both a green and a blue LED and a photodetector. Analysis region 30B is a flow cytometric analysis region optically coupled with a measurement apparatus comprising a diode laser and a plurality of photodetectors at various optical axis and collection cone angles.

The cartridge of FIG. 11 can be used for hematology. A single cartridge can determine the red cell count, the total hemoglobin, and the white cell count and characterization. The analysis requires only 15 $\mu$l of sample, and the waste fluid is contained within the cartridge for safe operation and disposability. The sample is loaded into the storage channel through inlet 10. At J1 the potentially contaminated leading edge of the sample flows in bypass channel 25 (FIG. 12), having a larger diameter than channel 20. Air in the channel escapes through vent 110A. The next segment of the sample fills the storage channel. Valve V4 is open and the sample flows to filling status indicator 30C. Vent 110C allows air to escape during sample loading. Excess sample flows into sample load bypass storage 115. The cartridge can be stored or transported prior to analysis. For measurement the cartridge is inserted into a measurement instrument having a cartridge holder and valve and pump mechanisms, which engage the valve and pump interfaces on the cartridge. The pump mechanisms comprise syringe pumps wherein the syringes are filled with reagents. The syringe connected to PI1 is filled with an inert driving fluid, the syringe connected to PI2 is filled with diluent, the syringe connected to PI3 is filled with a soft lysing agent, the syringe connected to PI4 is filled with a Drabkin lysing reagent and the syringe connected to PI5 is filled with a sheath fluid.

After insertion in the measurement apparatus, the sample is resuspended and analyzed. The entire measurement, including sample resuspension, can be performed in less than two minutes. The procedure for operating the analysis cartridge of FIG. 11 for hematology is outlined in Tables 1–3. For each time interval from t1 through t17, Table 1 describes the procedure, Table 2 gives the elapsed time, and Table 3 gives the status of valves and pumps fluidically connected to the cartridge and the status of optical measurement apparatus optically connected to the cartridge. In the first analysis time interval, t1, air is purged from resuspension pump interface PI1 through valve V5 into waste storage container 100. In t2 the reagent and sheath fluid channels are purged and wet. In t3 the optical path in absorption measurement region 30A is calibrated using the blue LED. In t4 the total hemoglobin sample segment between J1 and J3 is resuspended by alternating dispense and aspirate cycles using P1. In t5 the total hemoglobin assay is performed by mixing the blood with Drabkin reagent to lyse the red blood cells, and measuring the absorption in analysis region 30A. To create a bubble-free mixture in the analysis region, air is purged from channels 24A and 80A. Preferably the sample fluid and the reagent reach J2 simultaneously. Mixing channel 90A is designed to allow formation of the cyanomethahemoglobin complex.

Following hemoglobin absorption assay, flow cytometric analysis is performed. In time intervals t6, t7 and t8 the channels used in flow cytometric analysis are purged. To protect optical surfaces in the cytometric region from direct contact with the sample, sheath fluid is pumped through the region during the purge. The sheath flow is set to a low ratio to minimize fluid accumulation in the waste storage container during priming stages. In t9 the RBC sample segment between J5 and J6 is resuspended. In t10 and t11 the optical measuring apparatus is aligned and the flow is stabilized. In t12 and t13 the RBC flow cytometric assay is performed. In t14 the WBC sample segment between J3 and J5 is resuspended. In t15 a soft lysing reagent is added to the sample and time is allowed for mixing and reaction in mixing channel 90B. In t16 and t17 the WBC assay is performed. The total elapsed time is 1.75 minutes. Following analysis, the cartridge is disposed of.

Figure 12:
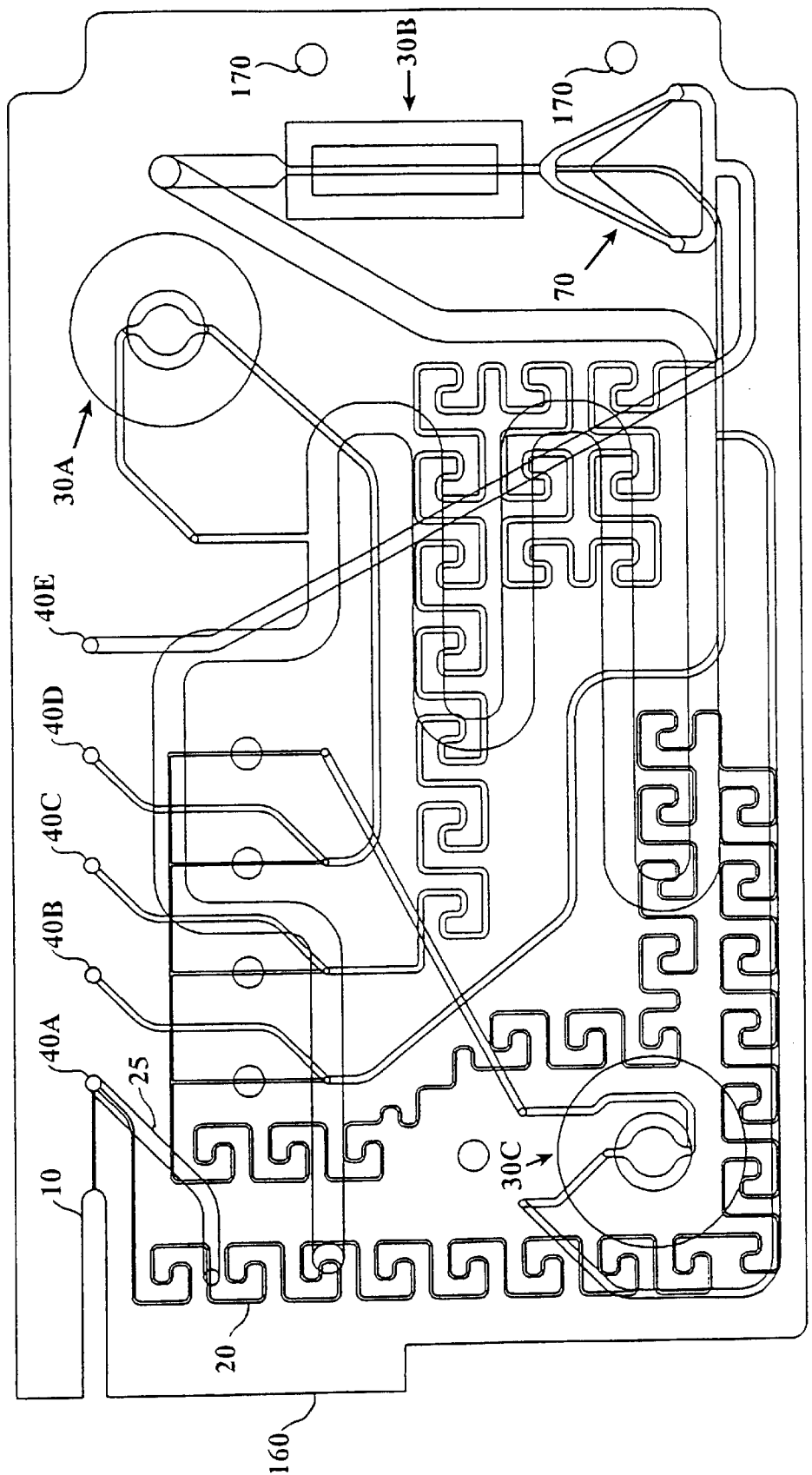
FIG. 12 is a plan view of an analysis cartridge having a convoluted storage channel, a plurality of reagent inlets, a convoluted mixing channel, a plurality of analysis regions, a plurality of valve and pump interfaces, and a waste storage channel.
Figure 13B:
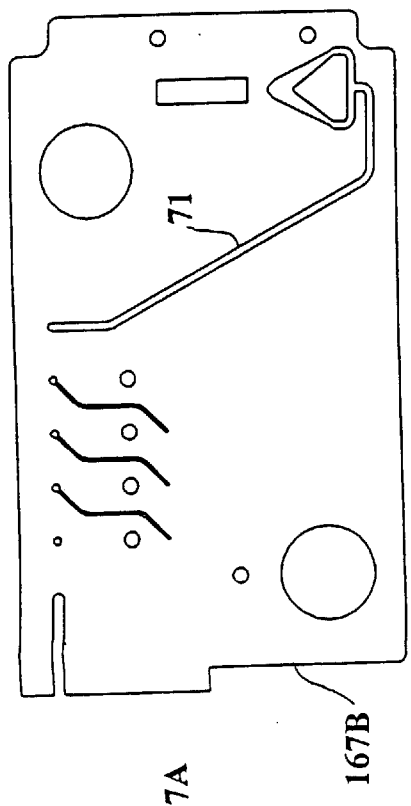
FIGS. 13A–G, shows the individual sheets which are laminated together to form the analysis cartridge of FIG. 12.
Figure 13D:
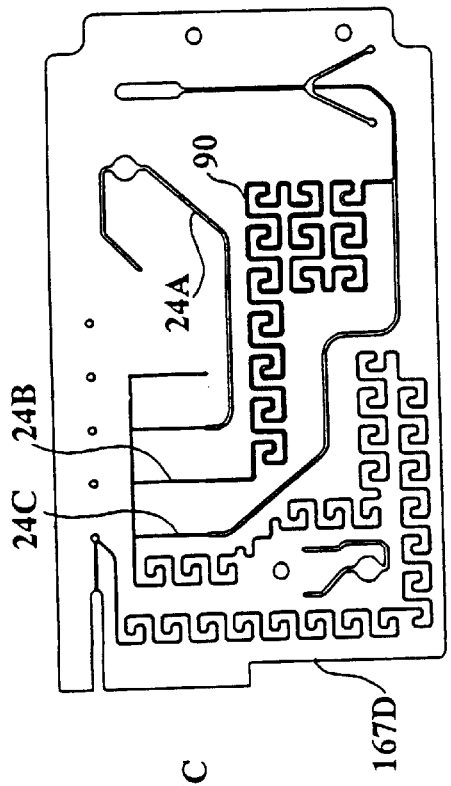
Figure 13A:
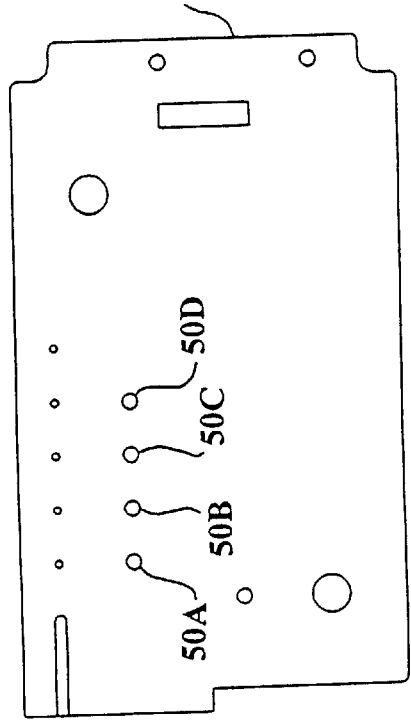
Figure 13C:
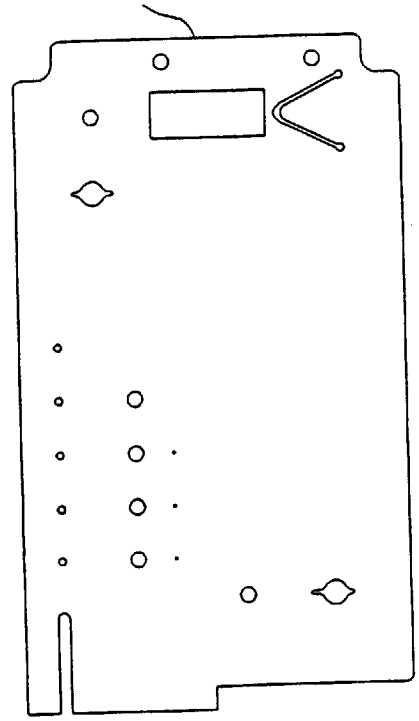
Figure 13E:
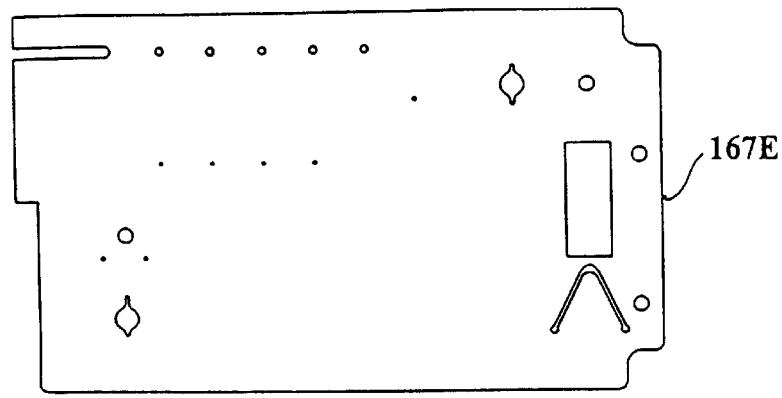
Figure 13F:
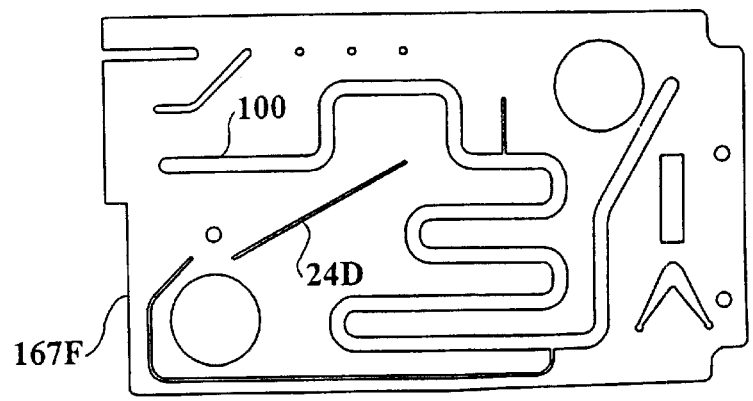
Figure 13G:
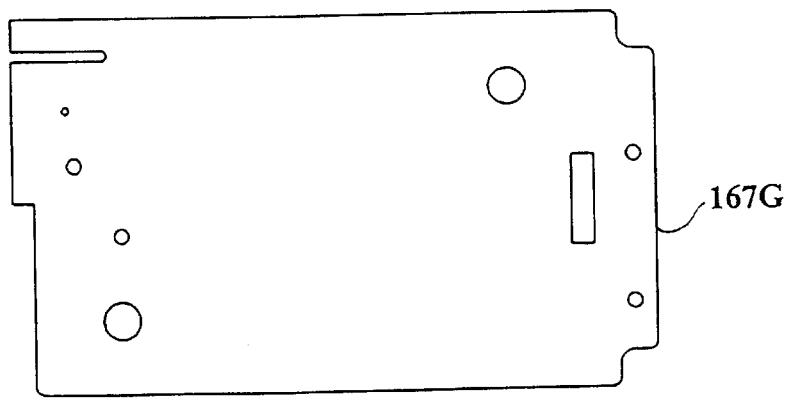

Drawings of a preferred embodiment of the hematology cartridge are shown in FIGS. 12 and 13. FIGS. 13A–G show the seven sheets, 167A–G, which are laminated together to form cartridge 160 shown in FIG. 12. This is a three-dimensional fluidic structure wherein channels in different layers appear to overlap in FIG. 12 but are in fact separated by sheets 167C and E. Vias in intervening sheets connect flow elements in different layers. Three-dimensional structures can be more compact and rugged than two-dimensional structures. Registry of the laminated sheets to the case is accomplished with holes 170 in the sheets. The case has pins that fit within holes 170. For measurement, the cartridge is inserted into a measurement instrument including a cartridge holder. The outer case of the cartridge (not shown) has alignment markings thereon for optical and fluidic alignment with the measurement apparatus. In this embodiment, the alignment markings are kinematic alignment markings comprising a pit, a groove and a flat. The cartridge holder has corresponding pins. The shape of the cartridge is designed for engagement with the cartridge holder, and thus in itself comprises an alignment marking.

Sample is introduced through inlet 10 and stored in channel 20. The sample leading edge flows into bypass channel 25. The bypass channel is fluidically connected to a case-mounted waste storage container (not shown). Syringe pump interfaces 40A–E and pinch valve interfaces 50A–D (FIG. 13A) control sample management in the cartridge. The syringe pump interfaces are also reagent inlets. When valve 50D is open sample flows through channel 24D (FIG. 13F) to filling status gauge 30C. For total hemoglobin assay lysing reagent is introduced through syringe pump interface 40D and the mixture flows through analysis channel 24A (FIG. 13D) to absorption analysis region 30A. For RBC assay, valve 50A is opened, diluent is introduced through syringe pump interface 40B, and the red blood cells are hydrodynamically focused in sheath flow assembly 70 and counted in flow cytometric analysis region 30B. For WBC assay, valve 50B is opened, a soft lysing agent, which masks red blood cells and platelets, is introduced through syringe pump interface 40C, mixing and reaction occur in mixing channel 90 (FIG. 13B), the sample is hydrodynamically focused in sheath flow assembly 70 and analyzed in flow cytometric analysis region 30B. Waste fluid from all three analysis regions flows into waste storage container 100 (FIG. 13F), which is fluidically connected with a case-mounted storage container having a vent therein. This waste storage container is a channel. It can alternatively or in addition be a fixed or expandable reservoir.

In this embodiment, storage channel 20 and mixing channel 90 are formed in sheet 167D. After cutting the sheet to form the channels, peninsulas of sheet material remain around the channels. The peninsulas are not well supported and can flop around during laminate assembly. A less floppy channel can be formed using two or more layers, with alternating loops of the channel formed in different layers.

The cartridge has been illustrated with particular mixing and measurement configurations. It can also provide filtering, diffusion based filtering as described in U.S. Pat. No. 5,932,100 issued Aug. 3, 1999, simultaneous particle separation and chemical reaction as described in U.S. Ser. No. 08/938,585 filed Sep. 26, 1997, valveless microswitching as described in U.S. Pat. No. 5,726,404, diffusion-based chemical sensing as described in U.S. Pat. No. 5,716,852, U.S. Pat. No. 5,948,684 issued Sep. 7,1999, and adsorption-enhanced differential extraction as described in U.S. Pat. No. 5,971,158 issued Oct. 26, 1999. The channel can also include fluidic elements for extraction, electrophoresis, electro-chemical reactions, chromatography and ion exchange reactions.

The cartridge can be fabricated from any moldable, machinable or etchable material. The term machining as used herein includes printing, stamping, cutting and laser ablating. The cartridge can be formed in a single sheet, in a pair of sheets sandwiched together, or in a plurality of sheets laminated together. The term "sheet" refers to any solid substrate, flexible or otherwise. The channels can be etched in a silicon substrate and covered with a cover sheet, which can be a transparent cover sheet. In a laminated embodiment, the channel walls are defined by removing material from a first sheet and the channel top and bottom are defined by laminating second and third sheets on either side of the first sheet. Any of the layers can contain fluid channels. In some cases the channel is simply a hole (or fluid via) to route the fluid to the next fluid laminate layer. Any two adjacent laminate layers may be permanently bonded together to form a more complex single part. Often fluidic elements that have been illustrated in two separate layers can be formed in a single layer.

Each layer of a laminate assembly can be formed of a different material. The layers are preferably fabricated from substantially rigid materials. A substantially rigid material is inelastic, preferably having a modulus of elasticity less than 1,000,000 psi, and more preferably less than 600,000 psi. Substantially rigid materials can still exhibit dramatic flexibility when produced in thin films. Examples of substantially rigid plastics include cellulose acetate, polycarbonate, methylmethacrylate and polyester. Metals and metal alloys are also substantially rigid. Examples include steels, aluminum, copper, etc. Glasses, silicon and ceramics are also substantially rigid.

To create the fluidic element in the sheets, material is removed to define the desired structure. The sheets can be machined using a laser to ablate the material from the channels. The material can be removed by traditional die cutting methods. For some materials chemical etching can be used. Alternatively, the negative of the structure desired can be manufactured as a mold and the structure can be produced by injection molding, vacuum thermoforming, pressure-assisted thermoforming or coining techniques.

The individual layers, assemblies of layers, or molded equivalents are bonded together using adhesives or welding. Alternatively, mechanical compression through the use of fasteners such as screws, rivets and snap-together assembly can be used to seal adjacent layers. Layers can be assembled using adhesives in the following ways. A rigid contact adhesive (for example, 3M1151) can be used to join adjacent layers. A solvent release adhesive may be used to chemically bond two adjacent players. An ultraviolet curing adhesive (for example, Loctite 3107) can be used to join adjacent layers when at least one layer is transparent in the ultraviolet. Precision applied epoxies, thermoset adhesives, and thermoplastic adhesives can also be used. Dry coatings that can be activated to bond using solvents, heat or mechanical compression can be applied to one or both surfaces. Layers can be welded together. For welding the layers preferably have similar glass transition temperatures and have mutual wetting and solubility characteristics. Layers can be welded using radio frequency dielectric heating, ultrasonic heating or local thermal heating.

The device of FIGS. 12 and 13 was fabricated as follows. Layers 167A and G were made of 4 mil mylar and layers 167C and E were made of 2 mil mylar. Layers 167B, D and F were made of 2 mil mylar with 3M1151 on both sides (4 mil inclusive). The adhesive had cover sheets thereon. With the cover sheets still on the adhesive, the sheets were laser ablated to machine flow elements therein. The cover sheets were removed and the individual laminate was assembled with the aid of an alignment jig.

This invention further includes a sample analysis instrument for use with an analysis cartridge, in particular a hematology analysis cartridge. The instrument has a cartridge holder, a flow cytometric measuring apparatus positioned to be coupled with a flow cytometric measuring region on the cartridge, and a second measuring apparatus positioned to be coupled with a second measuring region on the cartridge. The flow cytometric measuring apparatus comprises a light source, preferably a laser, and at least one photodetector. The photodetectors can be positioned for measuring small angle scattering, large angle scattering or fluorescence. The apparatus can also include optical elements such as focusing and collection lenses, wavelength filters, dichroic mirrors and polarizers. The second measuring apparatus can be any measuring apparatus including optical, electrical, pressure sensitive and flow sensitive apparatus. Absorption measuring apparatus comprising a light source and a photodetector is preferred. Preferably the light source is positioned on a first side of the cartridge holder and the photodetector is positioned on the opposite side.

Figure 14:
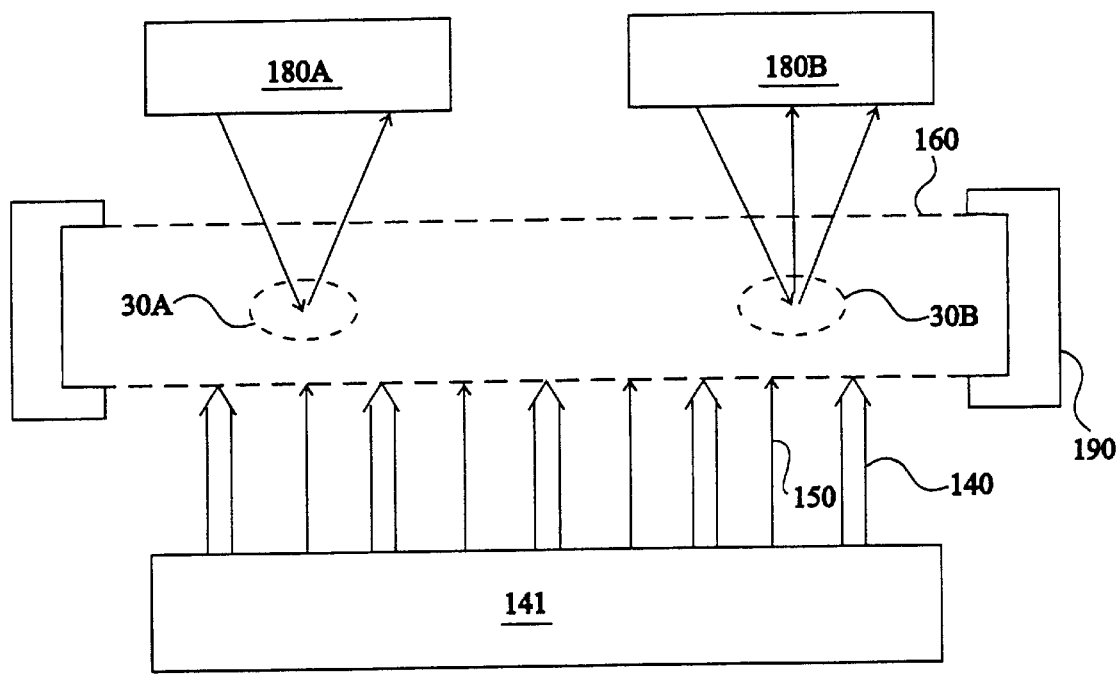
FIG. 14 is a sample analysis instrument for use with a fluidic cartridge.

A measurement instrument is shown schematically in FIG. 14. It comprises cartridge holder 190, flow cytometric measurement apparatus 180B and absorption measurement apparatus 180A. Cartridge 160, shown in phantom, slides into the cartridge holder. The measurement apparati are positioned to be optically coupled with flow cytometric analysis region 30B and absorption analysis region 30A. This instrument also includes pump and valve mechanism manifold 141. The pump mechanisms are syringe pumps which couple to pump interfaces on the cartridge via cannulas 140. The manifold can also include reagent reservoirs to refill the syringe pumps for multiple assays. The valve mechanisms activate valve pins 150, which couple to valve interfaces on the cartridge.

Preferably the cartridge holder has alignment markings thereon to mate with corresponding markings on the cartridge. The alignment markings can be the shape of the holder, protruding pins, notches, rods, kinematic mounts, two stage kinematic mounts as described in U.S. Pat. No. 5,748,827 issued May 5, 1998, or any other feature that facilitates positioning of the cartridge. In lieu of or in addition to cartridge alignment, the instrument can include optical steering elements, such as mirrors, to align the measuring apparatus with the analysis region. The analysis instrument can further include valve and pump mechanisms which couple with valve and pump interfaces on the cartridge.

All references cited herein are incorporated by reference in their entirety.

Preferred embodiments described above are intended to be illustrative of the spirit of this invention. Numerous variations and applications will be readily apparent to those skilled in the art. The range and scope of this patent is defined by the following claims.

TABLE 1

Time Interval Description

| | |
|---|---|
| t1 | Purge air from PI1 through valve V5. |
| t2 | Purge air and wet delivery lines from PI2 to J7; PI3 to J7; PI4 to J2; and P15 to J8 |
| t3 | THB optical path calibration using 430 nm blue LED and Drabkin reagent absorbtion. |
| t4 | THB Sample segment resuspension |
| t5 | Total hemaglobin assay; purge of air from J1 to J2 & uniform mixing of sample + Drabkin & creation of a bubble free mixture in flow cell. Time allowed for the creation of the Cyanomethahemaglobin complex. |
| t6 | RBC sample segment mis/air purge from J6 through J9&J7 to J8. Sheath pump is set to a low ratio, about 5:1 in order to protect optical surfaces of the cytometer section. |
| t7 | WBC sample segment mis/air purge from J3 through J4&J7 to j8. Sheath pump is set to a low ratio, about 5:1 in order to protect optical surfaces of the cytometer section. |
| t8 | J7 junction purge. Purge air from the region around J7 through the cytometer to waste. |
| t9 | RBC sample segment resuspension |
| t10 | Beam steering/optical targeting. |
| t11 | RBC assay flow stabilization algorithm based on mean pulse frequency PID feedback control |
| t12 | RBC assay. |
| t13 | Second RBC assay (if required) |
| t14 | WBC sample segment resuspension |
| t15 | WBC assay flow stabilization and 15 second time delay. |
| t16 | WBC assay. |
| t17 | Second WBC assay (if required) |

TABLE 2

| Time Interval | t1 | t2 | t3 | t4 | t5 | t6 | t7 | t8 | t9 | t10 | t11 | t12 | t13 | t14 | t15 | t16 | t17 |
|---|---|---|---|---|---|---|---|---|---|---|---|---|---|---|---|---|---|
| Interval time(s) | 1 | 3 | 2 | 3 | 10 | 2 | 2 | 1 | 3 | 5 | 4 | 4 | 3 | 1.6 | 17 | 22 | 22 |
| Elapsed time(s) | 1 | 4 | 6 | 9 | 19 | 21 | 23 | 24 | 27 | 32 | 36 | 40 | 43 | 45 | 62 | 83 | 105 |
| Elapsed time (min) | 0.02 | 0.07 | 0.10 | 0.15 | 0.32 | 0.35 | 0.38 | 0.40 | 0.45 | 0.53 | 0.60 | 0.67 | 0.72 | 0.74 | 1.03 | 1.39 | 1.75 |

TABLE 3

Resource Status

| Time interval | t1 | t2 | t3 | t4 | t5 | t6 | t7 | t8 | t9 | t10 | t11 | t12 | t13 | t14 | t15 | t16 | t17 |
|---|---|---|---|---|---|---|---|---|---|---|---|---|---|---|---|---|---|
| Resuspension pump, P1D (dispense) | X | | | X | X | X | X | | X | X | X | X | X | X | X | X | X |
| Resuspension pump, P1A (asperiate) | X | | | X | X | X | X | | X | X | X | X | X | X | X | X | X |
| Diluent pump, P2 | | X | | | X | | X | | X | X | X | X | X | X | | | |
| Soft Lyse pump, P3 | | X | | | | | X | X | | | | | | | X | X | X |
| THB pump, P4 | | X | X | X | X | | | | | | | | | | | | |
| Sheath pump, P5 | | X | | | | X | X | X | X | X | X | X | X | X | X | X | X |
| RBC Valve, V1 | C[1] | O | C | C | C | O | C | O | O | O | O | O | O | O | C | C | C |
| WBC Valve, V2 | C | O | C | C | C | C | O | O | C | C | C | C | C | C | O | O | O |
| THB Valve, V3 | C | O | C | O | O | C | C | C | C | C | C | C | C | C | C | C | C |
| Waste Isolation Valve, V4 | C | C | C | C | C | C | C | C | C | C | C | C | C | C | C | C | C |
| Sample delivery purge, V5 | O | C | C | C | C | C | C | C | C | C | C | C | C | C | C | C | C |
| Beam Steering Motor, M1 | | | | | | | | | | X | | | | | | | |
| Beam Steering Motor, M2 | | | | | | | | | | X | | | | | | | |
| Diode laser | | | | | | | | | | X | X | X | X | X | X | X | X |
| Green LED | | | | | X | | | | | | | | | | | | |
| Blue LED | | | X | | | | | | | | | | | | | | |

[1]C = Closed,
O = Open

We claim:

1. A method of fabricating a laminated fluidic flow cartridge comprising a sheath flow assembly having a sample flow channel, first and second sheath fluid channels positioned on either side of and converging with said sample flow channel, and upper and lower sheath fluid chambers positioned above and below and conversing with said sample flow channel, the method comprising the steps of:
  providing at least first, second and third rigid sheets, wherein the walls of said lower sheath fluid chamber are formed in said first rigid sheet, the walls of said sample flow channel and said first and second sheath fluid channels are formed in said second rigid sheet, and the walls of said upper sheath fluid chamber are formed in said third rigid sheet;
  providing an alignment hole within each of said rigid sheets;
  stacking said rigid sheets such that said alignment holes are aligned; and
  adhering abutting surfaces of said rigid sheets, thereby forming said laminated fluidic flow cartridge.

2. The method of claim 1 wherein said step of providing at least first, second and third rigid sheets further comprises the steps of:
  providing at least first, second and third rigid sheets; and
  machining the walls of said lower sheath fluid chamber in said first rigid sheet, the walls of said sample flow channel and said first and second sheath fluid channels in said second rigid sheet, and the walls of said upper sheath fluid chamber in said third rigid sheet.

3. The method of claim 2 wherein said step of machining is selected from the group consisting of laser ablating, cutting and die cutting.

4. The method of claim 1 wherein said rigid sheets are made by a process selected from the group consisting of injection molding, vacuum thermoforming, pressure-assisted thermoforming and coining.

5. The method of claim 1 wherein said rigid sheets are selected from the group consisting of cellulose acetate, polycarbonate, poymethylmethacrylate and polyester sheets.

6. The method of claim 1 wherein said step of adhering abutting surfaces of said rigid sheets uses an adhesive.

7. The method of claim 6 wherein said adhesive is selected from the group consisting of contact adhesives, solvent release adhesives, ultraviolet curing adhesives, epoxies, thermoset adhesives, thermoplastic adhesives and dry coating adhesives.

8. The method of claim 3 wherein at least alternate layers of said rigid sheets comprise rigid sheets coated with contact adhesive and wherein said step of machining comprises laser ablating or cutting.

9. The method of claim 8 wherein each of said rigid sheets coated with contact adhesive further comprises a cover sheet attached to said contact adhesive and wherein said method further comprises the step of removing said cover sheets after said step of machining laser ablation or cutting and prior to said step of stacking said rigid sheets.

10. The method of claim 9 wherein said rigid sheets are polyester sheets.

* * * * *

UNITED STATES PATENT AND TRADEMARK OFFICE
CERTIFICATE OF CORRECTION

PATENT NO. : 6,712,925 B1 Page 1 of 1
APPLICATION NO. : 09/428804
DATED : March 30, 2004
INVENTOR(S) : Mark R. Holl et al.

It is certified that error appears in the above-identified patent and that said Letters Patent is hereby corrected as shown below:

Title Page
Item (56) Cited Reference U.S. PATENT DOCUMENTS
" 4,794,485 12/1998 Bertolotti 356/318" should read as --5,793,485 8/11/98 Gourley 356/318--.

Column 15
Line 31, "conversing" should read as --converging--.

Column 16
Line 34, "poymethylmethacrylate" should read as --polymethylmethacrylate--.
Line 50, "machining laser ablation or cutting and" should read as --machining and--.

Signed and Sealed this

Twenty-fourth Day of October, 2006

JON W. DUDAS
*Director of the United States Patent and Trademark Office*